US008530416B2

(12) United States Patent
Seger et al.

(10) Patent No.: US 8,530,416 B2
(45) Date of Patent: *Sep. 10, 2013

(54) VARIANTS OF PIGMENT EPITHELIUM DERIVED FACTOR AND USES THEREOF

(75) Inventors: Rony Seger, Yavne (IL); Galia Maik-Rachline, Kfar Saba (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/438,783

(22) Filed: Apr. 3, 2012

(65) Prior Publication Data

US 2012/0184481 A1    Jul. 19, 2012

Related U.S. Application Data

(63) Continuation of application No. 11/718,873, filed as application No. PCT/IL2004/001052 on Nov. 16, 2004, now Pat. No. 8,173,591.

(51) Int. Cl.
*A61K 38/18* (2006.01)
*C07K 14/475* (2006.01)

(52) U.S. Cl.
USPC ......... 514/7.6; 514/13.3; 514/19.8; 514/21.2; 530/350

(58) Field of Classification Search
None
See application file for complete search history.

(56) References Cited

U.S. PATENT DOCUMENTS

| | | | |
|---|---|---|---|
| 4,816,567 | A | 3/1989 | Cabilly |
| 5,840,686 | A | 11/1998 | Chader |
| 6,319,687 | B1 | 11/2001 | Chader |
| 6,451,763 | B1 | 9/2002 | Tombran-Tink |
| 6,797,691 | B1 | 9/2004 | Bouck |
| 6,821,775 | B1 | 11/2004 | Kovesdi |
| 2003/0158112 | A1 | 8/2003 | Campochiaro |
| 2003/0216286 | A1 | 11/2003 | Bouck |
| 2004/0014664 | A1 | 1/2004 | Bouck |
| 2005/0148508 | A1 | 7/2005 | Shaltiel |
| 2005/0222031 | A1 | 10/2005 | Yamagishi |

FOREIGN PATENT DOCUMENTS

| | | |
|---|---|---|
| WO | 93/24529 | 12/1993 |
| WO | 95/33480 | 12/1995 |
| WO | 01/58494 | 8/2001 |
| WO | 03/059248 | 7/2003 |
| WO | 03/080648 | 10/2003 |
| WO | 2004/028559 | 4/2004 |
| WO | 2005/041887 | 5/2005 |

OTHER PUBLICATIONS

Abramson, Lisa P. et al., (2003) Wilms' tumor growth is suppressed by antiangiogenic pigment epithelium-derived factor in a xenograft model. J Pediatric Surgery 38(3):336-342.

Anderson, W. (1998) Human gene therapy. Nature 392(6679):25-30.
Appukuttan, B. et al., (2003) Evaluation of Amino Acid Polymorphisms within the PEDF Protein in the Normal Population and in Patients With AMD. Invest Opthalmol Vis Sci 44:E-Abstract 3086-B925.
Becerra, S. Patricia et al., (1995) Pigment epithelium-derived factor behaves like a noninhibitory serpin. Neurotrophic activity does not require the serpin reactive loop. J Biol Chem 270(43):25992-25999.
Berns, K. I. and Giraud, C. et al., (1995) Adenovirus and adeno-associated virus as vectors for gene therapy. Ann. N.Y. Acad. Sci. 772:95-104 Epub Dec. 17, 2006.
Dawson, D. W. et al., (1999) Pigment epithelium-derived factor: a potent inhibitor of angiogenesis. Science 285 (5425):245-248.
Federoff, Howard J. et al., (1992) Expression of nerve growth factor in vivo from a defective herpes simplex virus 1 vector prevents effects of axotomy on sympathetic ganglia. Proc Natl Acad Sci USA 89(5):1636-1640.
Fink, D. J. et al., (1996) Gene transfer to neurons using herpes simplex virus-based vectors. Ann. Rev. Neurosci. 19:265-287.
Gettins, Peter G. W. et al., (2002) Pigment epithelium-derived factor (PEDF), a serpin with potent anti-angiogenic and neurite outgrowth-promoting properties. Biol Chem 383:1677-1682.
Holmes, William E. et al., (1987) Primary structure of human alpha 2-antiplasmin, a serine protease inhibitor (serpin). J Biol Chem 262:1659-1664.
Huse, William D. et al., (1989) Generation of a large combinatorial library of the immunoglobulin repertoire in phage lambda.Science 246(4935):1275-1281.
Juengst, Eric T. (2003) What next for human gene therapy? Gene transfer often has multiple and unpredictable effects on cells.British Medical Journal 326(7404):1410-1411.
Kohler, G. and Milstein, C. (1976) Derivation of specific antibody-producing tissue culture and tumor lines by cell fusion. Eur. J. Immunol. 6(7):511-519.
Kozaki, Ken-Ichi et al., (1998) Isolation, purification, and characterization of a collagen-associated serpin, caspin, produced by murine colon adenocarcinoma cells. J Biol Chem 273(24):15125-15130.
Maik-Rachline (2004) The role of extracellular phosphorylation in the biological activities of pigment epithelium derived factor (PEDF). Thesis for the degree of Doctor in Philosophy.
Maik-Rachline, Galia et al., (2005) Extracellular phosphorylation converts pigment epithelium-derived factor from a neurotrophic to an antiangiogenic factor. Blood 105(2):670-678.
Maik-Rachline, Galia et al., (2006) Variable phosphorylation states of pigment-epithelium-derived factor differentially regulate its function. Blood 107(7):2745-2752.

(Continued)

*Primary Examiner* — Marianne P Allen
(74) *Attorney, Agent, or Firm* — Rodney J. Fuller; Booth Udall Fuller, PLC

(57) ABSTRACT

The present invention provides anti-angiogenic variants of pigment epithelium derived factor (PEDF) comprising at least one altered phosphorylation site, polynucleotides encoding same and uses thereof. Particularly, the present invention provides variants of human PEDF comprising at least one amino acid substitution at serine residues (24), (114), and (227). The PEDF variants are potent anti-angiogenic factors, and thus useful in treating diseases or disorders associated with neovascularization.

8 Claims, 13 Drawing Sheets

(56) References Cited

OTHER PUBLICATIONS

Maik-Rachline, Galia and Seger, Rony Extracellular Phosphorylation Converts PEDF From Neurotrophic to Antiangiogenic Factor. FEBS Lecture Course on Cellular Signaling. May 21-27, 2004.

Mural, Richard J. et al., (2002) A comparison of whole-genome shotgun-derived mouse chromosome 16 and the humen genome. Science 296(5573):1661-1671.

Passaniti, A. et al., (1992) A simple, quantitative method for assessing angiogenesis and antiangiogenic agents using reconstituted basement membrane, heparin, and fibroblast growth factor. Lab. Invest. 67(4):519-528.

Pignolo, Robert J. et al., (1993) Senescent WI-38 cells fail to express EPC-1, a gene induced in young cells upon entry into the G0 state. J of Biol Chem 268(12):8949-8957.

Rubanyi, Gabor (2001) The future of human gene therapy. Biol Aspects Med. 22(3):113-142.

Schulze, Andreas J. et al., (1990) Structural transition of alpha 1-antitrypsin by a peptide sequentially similar to beta-strand s4A. Eur J Biochem 194(1):51-56.

Seger, Rony et al., Intracellular Signaling Cascades. The Weizmann Institute BioScience Open Day. May 17, 2004.

Shirozu, Michio et al., (1996) Characterization of novel secreted and membrane proteins isolated by the signal sequence trap method. Genomics 37(3)273-280.

Singh, Vijay K. et al., (1998) Structural and comparative analysis of the mouse gene for pigment epithelium-derived factor (PEDF). Mol Vis 4:7.

Steele, F. R. el al., (1993) Pigment epithelium-derived factor: neurotrophic activity and identification as a member of the serine protease inhibitor gene family. Proc Natl Acad Sci U.S.A. 90(4):1526-1530.

Stellmach, Veronica et al., (2001) Prevention of ischemia-induced retinopathy by the natural ocular antiangiogenic agent pigment epithelium-derived factor. Proc Natl Acad Sci USA 98(5):2593-2597.

Tombran-Tink, Joyce et al., (1996) Organization, evolutionary conservation, expression and unusual Alu density of the human gene for pigment epithelium-derived factor, a unique neurotrophic serpin. Mol Vis 2:11.

Tombran-Tink, Joyce (2005) The neuroprotective and angiogenesis inhibitory serpin, PEDF: New insight into phylogeny, function, and signaling. Frontiers in Bioscience 10(S):2131-2149.

Verma, Inder M. and Somia, Nikunj (1997) Gene therapy—promises, problems and prospects. Nature 389 (6648):239-242.

Vosloglou-Nomikos, T. et al., (2003) Clinical predictive value of the in vitro cell line, human xenograft, and mouse allograft preclinical cancer models. Clin Cancer Res 9(11):4227-4239.

Ward E. Sally et al., (1989) Binding activities of a repertoire of single immunoglobulin variable domains secreted from *Escherichia coli*. Nature 341(6242):544-546.

Database Uniprot [online] Jul. 15, 1998 "Recname: Full=pigment epithelium-derived factor; short=PEDF; Altname: Full=Serpin F1; Altname: Full=stromal cell-derived factor 3; Short=SDF-3; Altname: Full=Caspin; Flags;Precurser;" retrieved from EBI accession No. UNIPORT:P97298.

Database Uniprot [online] May 10, 2005 "Subname:Full=Serine (or cysteine proteinase inhibitor, clade F, member 1; Subname:Full=Serine (or cysteine) peptidase inhibitor, clade F, member 1, isoform CRA_a;" XP002573504 retrieved from EBI accession No. Q5ND38.

Duh, Elia J. et al., (2002) Pigment Epithelium-Derived Factor Suppresses Ischemia-Induced Retinal Neovascularization and VEGF-Induced Migration and Growth. Invest Opthalmol Vis Sci 43(3):821-829.

EK, Eugene T. H. et al., (2006) Pigment epithelium-derived factor: a multimodal tumor inhibitor. Mol Cancer Ther 5 (7):1641-1646.

Konson, Alexander et al., (2010) Phosphomimetic mutants of pigment epithelium-derived factor with enhanced antiangiogenic activity as potent anticancer agents. Cancer Res 70(15):6247-6257 Epub Jul. 7, 2010.

Mori, Keisuke et al., (2002) Regression of ocular neovascularization in response to increased expression of pigment epithelium-derived factor. Invest Opthalmol Vis Sci 43(7):2428-2434.

Saishin, Yoshitsugu et al., (2005) Periocular gene transfer of pigment epithelium-derived factor inhibits choroidal neovascularization in a human-sized eye. Hum Gene Ther 16(4):473-478.

Petersen, Steen V. et al., "Pigment-epithelium-derived factor (PEDF) occurs at a physiologically relevant concentration in human blood: purification and characterization", Biochem J., 374(pt 1):199-266 (2003).

Redegeld, Frank A. et al., "Ecto-protein kinases: ecto-domain phosphorylation as a novel target for pharmacological manipulafion?", Trends Pharmacol. Sci., 20(11):453-459 (1999).

☒ Trytic peptides of the 20kDa fragment
☒ Trytic peptides of the 30kDa fragment
■ N-terminal sequence of the 30kDa fragment
♦ Putative CK2 phosphorylation site
♦ Glycosylation site

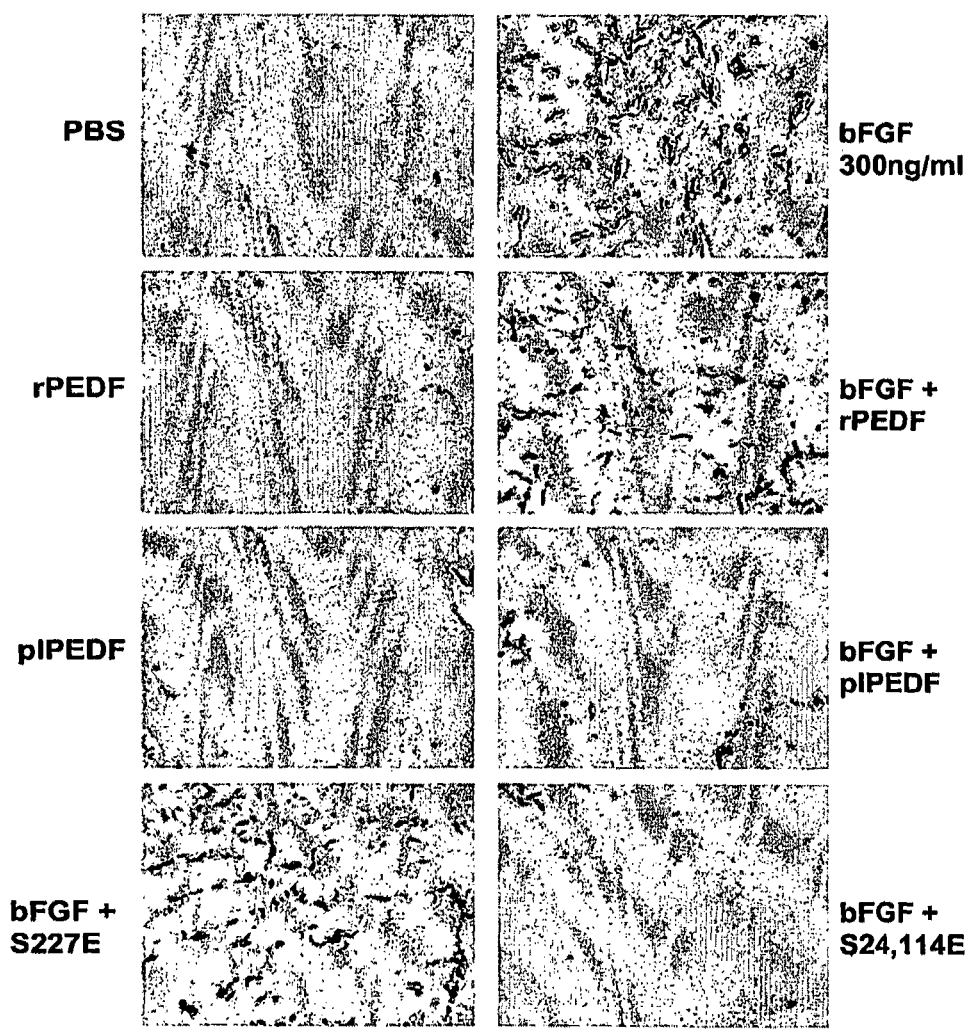

SEQUENCE LISTING

<160> NUMBER OF SEQ ID NOS: 22

<210> SEQ ID NO 1
<211> LENGTH: 418
<212> TYPE: PRT
<213> ORGANISM: Homo sapiens

<400> SEQUENCE: 1

```
Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Asp Pro Phe Phe Lys
        35                  40                  45

Val Pro Val Asn Lys Leu Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365
```

```
Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 2
<211> LENGTH: 418
<212> TYPE: PRT
<213> ORGANISM: Artificial Sequence
<220> FEATURE:
<223> OTHER INFORMATION: Synthetic protein

<400> SEQUENCE: 2

Met Gln Ala Leu Val Leu Leu Leu Cys Ile Gly Ala Leu Leu Gly His
1               5                   10                  15

Ser Ser Cys Gln Asn Pro Ala Glu Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
```

```
                305                 310                 315                 320
Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
                355                 360                 365

Ala Gly Thr Thr Pro Ser Pro Gly Leu Gln Pro Ala His Leu Thr Phe
                370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 3
<211> LENGTH: 418
<212> TYPE: PRT
<213> ORGANISM: Artificial Sequence
<220> FEATURE:
<223> OTHER INFORMATION: Synthetic protein

<400> SEQUENCE: 3

Met Gln Ala Leu Val Leu Leu Leu Cys Ile Gly Ala Leu Leu Gly His
1               5                   10                  15

Ser Ser Cys Gln Asn Pro Ala Ala Pro Pro Glu Glu Gly Ser Pro Asp
                20                  25                  30

Pro Asp Ser Thr Gly Ala Leu Val Glu Glu Glu Asp Pro Phe Phe Lys
                35                  40                  45

Val Pro Val Asn Lys Leu Ala Ala Ala Val Ser Asn Phe Gly Tyr Asp
            50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
                115                 120                 125

Val Thr Ala Pro Gln Lys Asn Leu Lys Ser Ala Ser Arg Ile Val Phe
            130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
            195                 200                 205

Gly Val Ala His Phe Lys Gly Gln Trp Val Thr Lys Phe Asp Ser Arg
            210                 215                 220

Lys Thr Ser Leu Glu Asp Phe Tyr Leu Asp Glu Arg Thr Val Arg
225                 230                 235                 240

Val Pro Met Met Ser Asp Pro Lys Ala Val Leu Arg Tyr Gly Leu Asp
                245                 250                 255
```

```
Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
            355                 360                 365

Ala Gly Thr Thr Pro Ser Pro Gly Leu Gln Pro Ala His Leu Thr Phe
            370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 4
<211> LENGTH: 418
<212> TYPE: PRT
<213> ORGANISM: Artificial Sequence
<220> FEATURE:
<223> OTHER INFORMATION: Synthetic protein
<220> FEATURE:
<221> NAME/KEY: MISC_FEATURE
<222> LOCATION: (24)..(24)
<223> OTHER INFORMATION: X = any amino acid substitution or any chemical
      modification of serine

<400> SEQUENCE: 4

Met Gln Ala Leu Val Leu Leu Leu Cys Ile Gly Ala Leu Leu Gly His
1               5                   10                  15

Ser Ser Cys Gln Asn Pro Ala Xaa Pro Pro Glu Glu Gly Ser Pro Asp
            20                  25                  30

Pro Asp Ser Thr Gly Ala Leu Val Glu Glu Asp Pro Phe Phe Lys
            35                  40                  45

Val Pro Val Asn Lys Leu Ala Ala Ala Val Ser Asn Phe Gly Tyr Asp
50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
            115                 120                 125

Val Thr Ala Pro Gln Lys Asn Leu Lys Ser Ala Ser Arg Ile Val Phe
            130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175
```

```
Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
            195                 200                 205

Gly Val Ala His Phe Lys Gly Gln Trp Val Thr Lys Phe Asp Ser Arg
210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
            245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
            290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
            325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
            355                 360                 365

Ala Gly Thr Thr Pro Ser Pro Gly Leu Gln Pro Ala His Leu Thr Phe
370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
            405                 410                 415

Gly Pro

<210> SEQ ID NO 5
<211> LENGTH: 418
<212> TYPE: PRT
<213> ORGANISM: Artificial Sequence
<220> FEATURE:
<223> OTHER INFORMATION: Synthetic protein

<400> SEQUENCE: 5

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Glu Ser Pro Asp Ile His Gly Thr Tyr Lys Glu Leu Leu Asp Thr
        115                 120                 125
```

```
Val Thr Ala Pro Gln Lys Asn Leu Lys Ser Ala Ser Arg Ile Val Phe
    130                 135                 140
Glu Lys Lys Leu Arg Ile Lys Ser Ser Phe Val Ala Pro Leu Glu Lys
145                 150                 155                 160
Ser Tyr Gly Thr Arg Pro Arg Val Leu Thr Gly Asn Pro Arg Leu Asp
                165                 170                 175
Leu Gln Glu Ile Asn Asn Trp Val Gln Ala Gln Met Lys Gly Lys Leu
            180                 185                 190
Ala Arg Ser Thr Lys Glu Ile Pro Asp Glu Ile Ser Ile Leu Leu Leu
        195                 200                 205
Gly Val Ala His Phe Lys Gly Gln Trp Val Thr Lys Phe Asp Ser Arg
    210                 215                 220
Lys Thr Ser Leu Glu Asp Phe Tyr Leu Asp Glu Glu Arg Thr Val Arg
225                 230                 235                 240
Val Pro Met Met Ser Asp Pro Lys Ala Val Leu Arg Tyr Gly Leu Asp
                245                 250                 255
Ser Asp Leu Ser Cys Lys Ile Ala Gln Leu Pro Leu Thr Gly Ser Met
            260                 265                 270
Ser Ile Ile Phe Phe Leu Pro Leu Lys Val Thr Gln Asn Leu Thr Leu
        275                 280                 285
Ile Glu Glu Ser Leu Thr Ser Glu Phe Ile His Asp Ile Asp Arg Glu
    290                 295                 300
Leu Lys Thr Val Gln Ala Val Leu Thr Val Pro Lys Leu Lys Leu Ser
305                 310                 315                 320
Tyr Glu Gly Glu Val Thr Lys Ser Leu Gln Glu Met Lys Leu Gln Ser
                325                 330                 335
Leu Phe Asp Ser Pro Asp Phe Ser Lys Ile Thr Gly Lys Pro Ile Lys
            340                 345                 350
Leu Thr Gln Val Glu His Arg Ala Gly Phe Glu Trp Asn Glu Asp Gly
        355                 360                 365
Ala Gly Thr Thr Pro Ser Pro Gly Leu Gln Pro Ala His Leu Thr Phe
    370                 375                 380
Pro Leu Asp Tyr His Leu Asn Gln Pro Phe Ile Phe Val Leu Arg Asp
385                 390                 395                 400
Thr Asp Thr Gly Ala Leu Leu Phe Ile Gly Lys Ile Leu Asp Pro Arg
                405                 410                 415
Gly Pro

<210> SEQ ID NO 6
<211> LENGTH: 418
<212> TYPE: PRT
<213> ORGANISM: Artificial Sequence
<220> FEATURE:
<223> OTHER INFORMATION: Synthetic protein

<400> SEQUENCE: 6

Met Gln Ala Leu Val Leu Leu Leu Cys Ile Gly Ala Leu Leu Gly His
1               5                   10                  15
Ser Ser Cys Gln Asn Pro Ala Ser Pro Pro Glu Glu Gly Ser Pro Asp
                20                  25                  30
Pro Asp Ser Thr Gly Ala Leu Val Glu Glu Asp Pro Phe Phe Lys
            35                  40                  45
Val Pro Val Asn Lys Leu Ala Ala Ala Val Ser Asn Phe Gly Tyr Asp
        50                  55                  60
Leu Tyr Arg Val Arg Ser Ser Met Ser Pro Thr Thr Asn Val Leu Leu
```

```
               65                  70                  75                  80
           Ser Pro Leu Ser Val Ala Thr Ala Leu Ser Ala Leu Ser Leu Gly Ala
                           85                  90                  95

Glu Gln Arg Thr Glu Ser Ile Ile His Arg Ala Leu Tyr Tyr Asp Leu
                          100                 105                 110

Ile Ala Ser Pro Asp Ile His Gly Thr Tyr Lys Glu Leu Leu Asp Thr
                          115                 120                 125

Val Thr Ala Pro Gln Lys Asn Leu Lys Ser Ala Ser Arg Ile Val Phe
                          130                 135                 140

Glu Lys Lys Leu Arg Ile Lys Ser Ser Phe Val Ala Pro Leu Glu Lys
           145                 150                 155                 160

Ser Tyr Gly Thr Arg Pro Arg Val Leu Thr Gly Asn Pro Arg Leu Asp
                          165                 170                 175

Leu Gln Glu Ile Asn Asn Trp Val Gln Ala Gln Met Lys Gly Lys Leu
                          180                 185                 190

Ala Arg Ser Thr Lys Glu Ile Pro Asp Glu Ile Ser Ile Leu Leu Leu
                          195                 200                 205

Gly Val Ala His Phe Lys Gly Gln Trp Val Thr Lys Phe Asp Ser Arg
                          210                 215                 220

Lys Thr Ser Leu Glu Asp Phe Tyr Leu Asp Glu Glu Arg Thr Val Arg
           225                 230                 235                 240

Val Pro Met Met Ser Asp Pro Lys Ala Val Leu Arg Tyr Gly Leu Asp
                          245                 250                 255

Ser Asp Leu Ser Cys Lys Ile Ala Gln Leu Pro Leu Thr Gly Ser Met
                          260                 265                 270

Ser Ile Ile Phe Phe Leu Pro Leu Lys Val Thr Gln Asn Leu Thr Leu
                          275                 280                 285

Ile Glu Glu Ser Leu Thr Ser Glu Phe Ile His Asp Ile Asp Arg Glu
                          290                 295                 300

Leu Lys Thr Val Gln Ala Val Leu Thr Val Pro Lys Leu Lys Leu Ser
           305                 310                 315                 320

Tyr Glu Gly Glu Val Thr Lys Ser Leu Gln Glu Met Lys Leu Gln Ser
                          325                 330                 335

Leu Phe Asp Ser Pro Asp Phe Ser Lys Ile Thr Gly Lys Pro Ile Lys
                          340                 345                 350

Leu Thr Gln Val Glu His Arg Ala Gly Phe Glu Trp Asn Glu Asp Gly
                          355                 360                 365

Ala Gly Thr Thr Pro Ser Pro Gly Leu Gln Pro Ala His Leu Thr Phe
                          370                 375                 380

Pro Leu Asp Tyr His Leu Asn Gln Pro Phe Ile Phe Val Leu Arg Asp
           385                 390                 395                 400

Thr Asp Thr Gly Ala Leu Leu Phe Ile Gly Lys Ile Leu Asp Pro Arg
                          405                 410                 415

Gly Pro

<210> SEQ ID NO 7
<211> LENGTH: 418
<212> TYPE: PRT
<213> ORGANISM: Artificial Sequence
<220> FEATURE:
<223> OTHER INFORMATION: Synthetic protein
<220> FEATURE:
<221> NAME/KEY: MISC_FEATURE
<222> LOCATION: (114)..(114)
<223> OTHER INFORMATION: X = any amino acid substitution or any chemical
      modification of serine
```

<400> SEQUENCE: 7

```
Met Gln Ala Leu Val Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Glu Asp Pro Phe Phe Lys
                35                  40                  45

Val Pro Val Asn Lys Leu Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110

Ile Xaa Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
            195                 200                 205

Gly Val Ala His Phe Lys Gly Gln Trp Val Thr Lys Phe Asp Ser Arg
210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
                260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
                355                 360                 365

Ala Gly Thr Thr Pro Ser Pro Gly Leu Gln Pro Ala His Leu Thr Phe
                370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415
```

Gly Pro

<210> SEQ ID NO 8
<211> LENGTH: 418
<212> TYPE: PRT
<213> ORGANISM: Artificial Sequence
<220> FEATURE:
<223> OTHER INFORMATION: Synthetic protein

<400> SEQUENCE: 8

```
Met Gln Ala Leu Val Leu Leu Cys Ile Gly Ala Leu Leu Gly His
1               5                   10                  15

Ser Ser Cys Gln Asn Pro Ala Glu Pro Glu Glu Gly Ser Pro Asp
                20                  25                  30

Pro Asp Ser Thr Gly Ala Leu Val Glu Glu Asp Pro Phe Phe Lys
            35                  40                  45

Val Pro Val Asn Lys Leu Ala Ala Val Ser Asn Phe Gly Tyr Asp
        50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110

Ile Glu Ser Pro Asp Ile His Gly Thr Tyr Lys Glu Leu Leu Asp Thr
            115                 120                 125

Val Thr Ala Pro Gln Lys Asn Leu Lys Ser Ala Ser Arg Ile Val Phe
        130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
            195                 200                 205

Gly Val Ala His Phe Lys Gly Gln Trp Val Thr Lys Phe Asp Ser Arg
        210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
                260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
        290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
            355                 360                 365
```

```
Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 9
<211> LENGTH: 418
<212> TYPE: PRT
<213> ORGANISM: Artificial Sequence
<220> FEATURE:
<223> OTHER INFORMATION: Synthetic protein

<400> SEQUENCE: 9

Met Gln Ala Leu Val Leu Leu Leu Cys Ile Gly Ala Leu Leu Gly His
1               5                   10                  15

Ser Ser Cys Gln Asn Pro Ala Ala Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65              70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ala Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
```

```
                      305                 310                 315                 320
Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 10
<211> LENGTH: 418
<212> TYPE: PRT
<213> ORGANISM: Artificial Sequence
<220> FEATURE:
<223> OTHER INFORMATION: Synthetic protein
<220> FEATURE:
<221> NAME/KEY: MISC_FEATURE
<222> LOCATION: (24)..(24)
<223> OTHER INFORMATION: X = any amino acid substitution or any chemical
      modification of serine
<220> FEATURE:
<221> NAME/KEY: MISC_FEATURE
<222> LOCATION: (114)..(114)
<223> OTHER INFORMATION: X = any amino acid substitution or any chemical
      modification of serine

<400> SEQUENCE: 10

Met Gln Ala Leu Val Leu Leu Cys Ile Gly Ala Leu Leu Gly His
1               5                   10                  15

Ser Ser Cys Gln Asn Pro Ala Xaa Pro Pro Glu Glu Gly Ser Pro Asp
                20                  25                  30

Pro Asp Ser Thr Gly Ala Leu Val Glu Glu Asp Pro Phe Phe Lys
            35                  40                  45

Val Pro Val Asn Lys Leu Ala Ala Ala Val Ser Asn Phe Gly Tyr Asp
50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Xaa Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205
```

Gly Val Ala His Phe Lys Gly Gln Trp Val Thr Lys Phe Asp Ser Arg
            210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
            245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
            290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
            325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
            355                 360                 365

Ala Gly Thr Thr Pro Ser Pro Gly Leu Gln Pro Ala His Leu Thr Phe
            370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                    405                 410                 415

Gly Pro

<210> SEQ ID NO 11
<211> LENGTH: 418
<212> TYPE: PRT
<213> ORGANISM: Artificial Sequence
<220> FEATURE:
<223> OTHER INFORMATION: Synthetic protein

<400> SEQUENCE: 11

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys

```
                145                 150                 155                 160
Ser Tyr Gly Thr Arg Pro Arg Val Leu Thr Gly Asn Pro Arg Leu Asp
                    165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
                195                 200                 205

Gly Val Ala His Phe Lys Gly Gln Trp Val Thr Lys Phe Asp Ser Arg
            210                 215                 220

Lys Thr Glu Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                    245                 250                 255

Ser Asp Leu Ser Cys Lys Ile Ala Gln Leu Pro Leu Thr Gly Ser Met
                260                 265                 270

Ser Ile Ile Phe Phe Leu Pro Leu Lys Val Thr Gln Asn Leu Thr Leu
                275                 280                 285

Ile Glu Glu Ser Leu Thr Ser Glu Phe Ile His Asp Ile Asp Arg Glu
            290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                    325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
                355                 360                 365

Ala Gly Thr Thr Pro Ser Pro Gly Leu Gln Pro Ala His Leu Thr Phe
            370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                    405                 410                 415

Gly Pro

<210> SEQ ID NO 12
<211> LENGTH: 418
<212> TYPE: PRT
<213> ORGANISM: Artificial Sequence
<220> FEATURE:
<223> OTHER INFORMATION: Synthetic protein

<400> SEQUENCE: 12

Met Gln Ala Leu Val Leu Leu Cys Ile Gly Ala Leu Leu Gly His
1               5                   10                  15

Ser Ser Cys Gln Asn Pro Ala Ser Pro Pro Glu Glu Gly Ser Pro Asp
                20                  25                  30

Pro Asp Ser Thr Gly Ala Leu Val Glu Glu Asp Pro Phe Phe Lys
                35                  40                  45

Val Pro Val Asn Lys Leu Ala Ala Val Ser Asn Phe Gly Tyr Asp
            50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95
```

-continued

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
            115                 120                 125

Val Thr Ala Pro Gln Lys Asn Leu Lys Ser Ala Ser Arg Ile Val Phe
        130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
210                 215                 220

Lys Thr Ala Leu Glu Asp Phe Tyr Leu Asp Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 13
<211> LENGTH: 418
<212> TYPE: PRT
<213> ORGANISM: Artificial Sequence
<220> FEATURE:
<223> OTHER INFORMATION: Synthetic protein
<220> FEATURE:
<221> NAME/KEY: MISC_FEATURE
<222> LOCATION: (227)..(227)
<223> OTHER INFORMATION: X = any amino acid substitution or any chemical modification of serine

<400> SEQUENCE: 13

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
             20                  25                  30

Pro Asp Ser Thr Gly Ala Leu Val Glu Glu Asp Pro Phe Phe Lys
         35                  40                  45

Val Pro Val Asn Lys Leu Ala Ala Val Ser Asn Phe Gly Tyr Asp
 50                  55                  60

Leu Tyr Arg Val Arg Ser Ser Met Ser Pro Thr Thr Asn Val Leu Leu
 65                  70                  75                  80

Ser Pro Leu Ser Val Ala Thr Ala Leu Ser Ala Leu Ser Leu Gly Ala
                 85                  90                  95

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
            115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
    195                 200                 205

Gly Val Ala His Phe Lys Gly Gln Trp Val Thr Lys Phe Asp Ser Arg
210                 215                 220

Lys Thr Xaa Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
    275                 280                 285

Ile Glu Glu Ser Leu Thr Ser Glu Phe Ile His Asp Ile Asp Arg Glu
290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
    355                 360                 365

Ala Gly Thr Thr Pro Ser Pro Gly Leu Gln Pro Ala His Leu Thr Phe
370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 14
<211> LENGTH: 1257

<212> TYPE: DNA
<213> ORGANISM: Homo sapiens

<400> SEQUENCE: 14

```
atgcaggccc tggtgctact cctctgcatt ggagccctcc tcgggcacag cagctgccag      60
aaccctgcca gccccccgga ggaaggctcc ccagaccccg acagcacagg ggcgctggtg     120
gaggaggagg atcctttctt caaagtcccc gtgaacaagc tggcagcggc tgtctccaac     180
ttcggctatg acctgtaccg ggtgcgatcc agcatgagcc ccacgaccaa cgtgctcctg     240
tctcctctca gtgtggccac ggccctctcg gccctctcgc tgggagcgga gcagcgaaca     300
gaatccatca ttcaccgggc tctctactat gacttgatca gcagcccaga catccatggt     360
acctataagg agctccttga cacggtcact gccccccaga gaacctcaa gagtgcctcc      420
cggatcgtct ttgagaagaa gctgcgcata aaatccagct ttgtggcacc tctggaaaag     480
tcatatggga ccaggcccag agtcctgacg ggcaaccctc gcttggacct gcaagagatc     540
aacaactggg tgcaggcgca gatgaaaggg aagctcgcca ggtccacaaa ggaaattccc     600
gatgagatca gcattctcct tctcggtgtg gcgcacttca aggggcagtg ggtaacaaag     660
tttgactcca gaaagacttc cctcgaggat ttctacttgg atgaagagag gaccgtgagg     720
gtccccatga tgtcggaccc taaggctgtt ttacgctatg gcttggattc agatctcagc     780
tgcaagattg cccagctgcc cttgaccgga agcatgagta tcatcttctt cctgccctg      840
aaagtgaccc agaatttgac cttgatagag gagagcctca cctccgagtt cattcatgac     900
atagaccgag aactgaagac cgtgcaggcg gtcctcactg tccccaagct gaagctgagt     960
tacgaaggcg aagtcaccaa gtccctgcag gagatgaagc tgcaatcctt gtttgattca    1020
ccagacttta gcaagatcac aggcaaaccc atcaagctga ctcaggtgga acaccgggct    1080
ggctttgagt ggaacgagga tgggcggga accaccccca gcccagggct gcagcctgcc    1140
cacctcacct cccgctgga ctatcacctt aaccagcctt tcatcttcgt actgagggac    1200
acagacacag gggcccttct cttcattggc aagattctgg accccagggg cccctaa     1257
```

<210> SEQ ID NO 15
<211> LENGTH: 1257
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (72)..(72)
<223> OTHER INFORMATION: n = G or A

<400> SEQUENCE: 15

```
atgcaggccc tggtgctact cctctgcatt ggagccctcc tcgggcacag cagctgccag      60
aaccctgccg anccccgga ggaaggctcc ccagaccccg acagcacagg ggcgctggtg     120
gaggaggagg atccttctt caaagtcccc gtgaacaagc tggcagcggc tgtctccaac     180
ttcggctatg acctgtaccg ggtgcgatcc agcatgagcc ccacgaccaa cgtgctcctg     240
tctcctctca gtgtggccac ggccctctcg gccctctcgc tgggagcgga gcagcgaaca     300
gaatccatca ttcaccgggc tctctactat gacttgatca gcagcccaga catccatggt     360
acctataagg agctccttga cacggtcact gccccccaga gaacctcaa gagtgcctcc      420
cggatcgtct ttgagaagaa gctgcgcata aaatccagct ttgtggcacc tctggaaaag     480
tcatatggga ccaggcccag agtcctgacg ggcaaccctc gcttggacct gcaagagatc     540
aacaactggg tgcaggcgca gatgaaaggg aagctcgcca ggtccacaaa ggaaattccc     600
```

```
gatgagatca gcattctcct tctcggtgtg gcgcacttca aggggcagtg ggtaacaaag      660
tttgactcca gaaagacttc cctcgaggat ttctacttgg atgaagagag gaccgtgagg      720
gtccccatga tgtcggaccc taaggctgtt ttacgctatg gcttggattc agatctcagc      780
tgcaagattg cccagctgcc cttgaccgga agcatgagta tcatcttctt cctgcccctg      840
aaagtgaccc agaatttgac cttgatagag gagagcctca cctccgagtt cattcatgac      900
atagaccgag aactgaagac cgtgcaggcg gtcctcactg tccccaagct gaagctgagt      960
tacgaaggcg aagtcaccaa gtccctgcag gagatgaagc tgcaatcctt gtttgattca     1020 ccagactta gcaagatcac aggcaaaccc atcaagctga ctcaggtgga acaccgggct     1080
ggctttgagt ggaacgagga tggggcggga accaccccca gcccagggct gcagcctgcc     1140
cacctcacct tcccgctgga ctatcacctt aaccagcctt tcatcttcgt actgagggac     1200
acagacacag ggcccttct cttcattggc aagattctgg accccagggg cccctaa      1257
```

<210> SEQ ID NO 16
<211> LENGTH: 1257
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (342)..(342)
<223> OTHER INFORMATION: n = A or G

<400> SEQUENCE: 16

```
atgcaggccc tggtgctact cctctgcatt ggagccctcc tcgggcacag cagctgccag       60
aaccctgcca gccccccgga ggaaggctcc ccagaccccg acagcacagg ggcgctggtg      120
gaggaggagg atcctttctt caaagtcccc gtgaacaagc tggcagcggc tgtctccaac      180
ttcggctatg acctgtaccg ggtgcgatcc agcatgagcc ccacgaccaa cgtgctcctg      240
tctcctctca gtgtggccac ggccctctcg gccctctcgc tgggagcgga gcagcgaaca      300
gaatccatca ttcaccgggc tctctactat gacttgatcg anagcccaga catccatggt      360
acctataagg agctccttga cacggtcact gcccccaga agaacctcaa gagtgcctcc      420
cggatcgtct ttgagaagaa gctgcgcata aaatccagct ttgtggcacc tctgaaaaag      480
tcatatggga ccaggcccag agtcctgacg ggcaaccctc gcttggacct gcaagagatc      540
aacaactggg tgcaggcgca gatgaaaggg aagctcgcca ggtccacaaa ggaaattccc      600
gatgagatca gcattctcct tctcggtgtg gcgcacttca aggggcagtg ggtaacaaag      660
tttgactcca gaaagacttc cctcgaggat ttctacttgg atgaagagag gaccgtgagg      720
gtccccatga tgtcggaccc taaggctgtt ttacgctatg gcttggattc agatctcagc      780
tgcaagattg cccagctgcc cttgaccgga agcatgagta tcatcttctt cctgcccctg      840
aaagtgaccc agaatttgac cttgatagag gagagcctca cctccgagtt cattcatgac      900
atagaccgag aactgaagac cgtgcaggcg gtcctcactg tccccaagct gaagctgagt      960
tacgaaggcg aagtcaccaa gtccctgcag gagatgaagc tgcaatcctt gtttgattca     1020 ccagactta gcaagatcac aggcaaaccc atcaagctga ctcaggtgga acaccgggct     1080
ggctttgagt ggaacgagga tggggcggga accaccccca gcccagggct gcagcctgcc     1140
cacctcacct tcccgctgga ctatcacctt aaccagcctt tcatcttcgt actgagggac     1200
acagacacag ggcccttct cttcattggc aagattctgg accccagggg cccctaa      1257
```

<210> SEQ ID NO 17
<211> LENGTH: 1257
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (72)..(72)
<223> OTHER INFORMATION: n = A or G
<220> FEATURE:
<221> NAME/KEY: misc_feature
<222> LOCATION: (342)..(342)
<223> OTHER INFORMATION: n = A or G

<400> SEQUENCE: 17

```
atgcaggccc tggtgctact cctctgcatt ggagccctcc tcgggcacag cagctgccag      60
aaccctgccg anccccggga ggaaggctcc ccagaccccg acagcacagg ggcgctggtg     120
gaggaggagg atcctttctt caaagtcccc gtgaacaagc tggcagcggc tgtctccaac     180
ttcggctatg acctgtaccg ggtgcgatcc agcatgagcc ccacgaccaa cgtgctcctg     240
tctcctctca gtgtggccac ggccctctcg gccctctcgc tgggagcgga gcagcgaaca     300
gaatccatca ttcaccgggc tctctactat gacttgatcg anagcccaga catccatggt     360
acctataagg agctccttga cacggtcact gcccccagaa gaacctcaa gagtgcctcc     420
cggatcgtct ttgagaagaa gctgcgcata aaatccagct ttgtggcacc tctggaaaag     480
tcatatggga ccaggcccag agtcctgacg gcaaccctc gcttggacct gcaagagatc     540
aacaactggg tgcaggcgca gatgaaaggg aagctcgcca ggtccacaaa ggaaattccc     600
gatgagatca gcattctcct tctcggtgtg gcgcacttca aggggcagtg ggtaacaaag     660
tttgactcca gaaagacttc cctcgaggat ttctacttgg atgaagagag gaccgtgagg     720
gtccccatga tgtcggaccc taaggctgtt ttacgctatg gcttggattc agatctcagc     780
tgcaagattg cccagctgcc cttgaccgga agcatgagta tcatcttctt cctgccctg     840
aaagtgaccc cgaatttgac cttgatagag gagagcctca cctccgagtt cattcatgac     900
atagaccgag aactgaagac cgtgcaggcg gtcctcactg tccccaagct gaagctgagt     960
tacgaaggcg aagtcaccaa gtccctgcag gagatgaagc tgcaatcctt gtttgattca    1020
ccagacttta gcaagatcac aggcaaaccc atcaagctga ctcaggtgga acaccgggct    1080
ggctttgagt ggaacgagga tgggcgggaa ccaccccca gccagggct gcagcctgcc    1140
cacctcacct cccgctgga ctatcacctt aaccagcctt tcatcttcgt actgagggac    1200
acagacacag gggcccttct cttcattggc aagattctgg accccagggg cccctaa    1257
```

<210> SEQ ID NO 18
<211> LENGTH: 1257
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (72)..(72)
<223> OTHER INFORMATION: n = C, A, G, or T

<400> SEQUENCE: 18

```
atgcaggccc tggtgctact cctctgcatt ggagccctcc tcgggcacag cagctgccag      60
aaccctgccg cnccccggga ggaaggctcc ccagaccccg acagcacagg ggcgctggtg     120
gaggaggagg atcctttctt caaagtcccc gtgaacaagc tggcagcggc tgtctccaac     180
ttcggctatg acctgtaccg ggtgcgatcc agcatgagcc ccacgaccaa cgtgctcctg     240
```

```
tctcctctca gtgtggccac ggccctctcg gccctctcgc tgggagcgga gcagcgaaca        300
gaatccatca ttcaccgggc tctctactat gacttgatca gcagcccaga catccatggt        360
acctataagg agctccttga cacggtcact gccccccaga agaacctcaa gagtgcctcc        420
cggatcgtct ttgagaagaa gctgcgcata aaatccagct ttgtggcacc tctggaaaag        480
tcatatggga ccaggcccag agtcctgacg ggcaaccctc gcttggacct gcaagagatc        540
aacaactggg tgcaggcgca gatgaaaggg aagctcgcca ggtccacaaa ggaaattccc        600
gatgagatca gcattctcct tctcggtgtg gcgcacttca agggcagtg ggtaacaaag         660 tttgactcca gaaagacttc cctcgaggat ttctacttgg atgaagagag gaccgtgagg        720
gtccccatga tgtcggaccc taaggctgtt ttacgctatg gcttggattc agatctcagc       780
tgcaagattg cccagctgcc cttgaccgga agcatgagta tcatcttctt cctgcccctg       840
aaagtgaccc agaatttgac cttgatagag gagagcctca cctccgagtt cattcatgac       900
atagaccgag aactgaagac cgtgcaggcg gtcctcactg tccccaagct gaagctgagt       960
tacgaaggcg aagtcaccaa gtccctgcag gagatgaagc tgcaatcctt gtttgattca      1020
ccagacttta gcaagatcac aggcaaaccc atcaagctga ctcaggtgga acaccgggct      1080
ggctttgagt ggaacgagga tggggcggga accacccca gcccagggct gcagcctgcc      1140
cacctcacct tcccgctgga ctatcaccct aaccagcctt tcatcttcgt actgagggac      1200
acagacacag ggcccttct cttcattggc aagattctgg accccagggg cccctaa          1257
```

<210> SEQ ID NO 19
<211> LENGTH: 1257
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (342)..(342)
<223> OTHER INFORMATION: n = C, A, G, or T

<400> SEQUENCE: 19

```
atgcaggccc tggtgctact cctctgcatt ggagccctcc tcgggcacag cagctgccag         60
aaccctgcca gcccccggga ggaaggctcc ccagaccccg acagcacagg ggcgctggtg       120
gaggaggagg atcctttctt caaagtcccc gtgaacaagc tggcagcggc tgtctccaac       180
ttcggctatg acctgtaccg ggtgcgatcc agcatgagcc ccacgaccaa cgtgctcctg       240
tctcctctca gtgtggccac ggccctctcg gccctctcgc tgggagcgga gcagcgaaca       300
gaatccatca ttcaccgggc tctctactat gacttgatcg cnagcccaga catccatggt      360
acctataagg agctccttga cacggtcact gccccccaga agaacctcaa gagtgcctcc      420
cggatcgtct ttgagaagaa gctgcgcata aaatccagct ttgtggcacc tctggaaaag      480
tcatatggga ccaggcccag agtcctgacg ggcaaccctc gcttggacct gcaagagatc      540
aacaactggg tgcaggcgca gatgaaaggg aagctcgcca ggtccacaaa ggaaattccc      600
gatgagatca gcattctcct tctcggtgtg gcgcacttca agggcagtg ggtaacaaag       660 tttgactcca gaaagacttc cctcgaggat ttctacttgg atgaagagag gaccgtgagg      720
gtccccatga tgtcggaccc taaggctgtt ttacgctatg gcttggattc agatctcagc     780
tgcaagattg cccagctgcc cttgaccgga agcatgagta tcatcttctt cctgcccctg     840
aaagtgaccc agaatttgac cttgatagag gagagcctca cctccgagtt cattcatgac     900
atagaccgag aactgaagac cgtgcaggcg gtcctcactg tccccaagct gaagctgagt     960
```

-continued

```
tacgaaggcg aagtcaccaa gtccctgcag gagatgaagc tgcaatcctt gtttgattca   1020
ccagacttta gcaagatcac aggcaaaccc atcaagctga ctcaggtgga acaccgggct   1080
ggctttgagt ggaacgagga tggggcggga accaccccca gcccagggct gcagcctgcc   1140
cacctcacct tcccgctgga ctatcacctt aaccagcctt tcatcttcgt actgagggac   1200
acagacacag gggcccttct cttcattggc aagattctgg accccagggg cccctaa     1257
```

<210> SEQ ID NO 20
<211> LENGTH: 1257
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (72)..(72)
<223> OTHER INFORMATION: n = C, A, G, or T
<220> FEATURE:
<221> NAME/KEY: misc_feature
<222> LOCATION: (342)..(342)
<223> OTHER INFORMATION: n = C, A, G, or T
<400> SEQUENCE: 20

```
atgcaggccc tggtgctact cctctgcatt ggagccctcc tcgggcacag cagctgccag    60
aaccctgccg cnccccgga ggaaggctcc ccagaccccg acagcacagg ggcgctggtg    120
gaggaggagg atcctttctt caaagtcccc gtgaacaagc tggcagcggc tgtctccaac   180
ttcggctatg acctgtaccg ggtgcgatcc agcatgagcc ccacgaccaa cgtgctcctg   240
tctcctctca gtgtggccac ggccctctcg gccctctcgc tgggagcgga gcagcgaaca   300
gaatccatca ttcaccgggc tctctactat gacttgatcg cnagcccaga catccatggt   360
acctataagg agctccttga cacggtcact gccccccaga agaacctcaa gagtgcctcc   420
cggatcgtct ttgagaagaa gctgcgcata aaatccagct ttgtggcacc tctggaaaag   480
tcatatggga ccaggcccag agtcctgacg gcaaccctc gcttggacct gcaagagatc    540
aacaactggg tgcaggcgca gatgaaaggg aagctcgcca ggtccacaaa ggaaattccc   600
gatgagatca gcattctcct tctcggtgtg gcgcacttca aggggcagtg ggtaacaaag   660
tttgactcca gaaagacttc cctcgaggat ttctacttgg atgaagagag gaccgtgagg   720
gtccccatga tgtcggaccc taaggctgtt ttacgctatg gcttggattc agatctcagc   780
tgcaagattg cccagctgcc cttgaccgga agcatgagta tcatcttctt cctgcccctg   840
aaagtgaccc agaatttgac cttgatagag gagagcctca cctccgagtt cattcatgac   900
atagaccgag aactgaagac cgtgcaggcg gtcctcactg tccccaagct gaagctgagt   960
tacgaaggcg aagtcaccaa gtccctgcag gagatgaagc tgcaatcctt gtttgattca   1020
ccagacttta gcaagatcac aggcaaaccc atcaagctga ctcaggtgga acaccgggct   1080
ggctttgagt ggaacgagga tggggcggga accaccccca gcccagggct gcagcctgcc   1140
cacctcacct tcccgctgga ctatcacctt aaccagcctt tcatcttcgt actgagggac   1200
acagacacag gggcccttct cttcattggc aagattctgg accccagggg cccctaa     1257
```

<210> SEQ ID NO 21
<211> LENGTH: 1257
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature

```
<222> LOCATION: (681)..(681)
<223> OTHER INFORMATION: n = C, A, G, or T

<400> SEQUENCE: 21
atgcaggccc tggtgctact cctctgcatt ggagccctcc tcgggcacag cagctgccag      60
aaccctgcca gccccccgga ggaaggctcc ccagaccccg acagcacagg ggcgctggtg     120
gaggaggagg atcctttctt caaagtcccc gtgaacaagc tggcagcggc tgtctccaac     180
ttcggctatg acctgtaccg ggtgcgatcc agcatgagcc ccacgaccaa cgtgctcctg     240
tctcctctca gtgtggccac ggccctctcg gccctctcgc tgggagcgga gcagcgaaca     300
gaatccatca ttcaccgggc tctctactat gacttgatca gcagcccaga catccatggt     360
acctataagg agctccttga cacggtcact gccccccaga gaacctcaa  gagtgcctcc     420 cggatcgtct ttgagaagaa gctgcgcata aaatccagct ttgtggcacc tctggaaaag     480
tcatatggga ccaggcccag agtcctgacg ggcaaccctc gcttggacct gcaagagatc     540
aacaactggg tgcaggcgca gatgaaaggg aagctcgcca ggtccacaaa ggaaattccc     600
gatgagatca gcattctcct ctccggtgtg gcgcacttca aggggcagtg ggtaacaaag     660
tttgactcca gaaagactgc nctcgaggat ttctacttgg atgaagagag gaccgtgagg     720
gtccccatga tgtcggaccc taaggctgtt ttacgctatg gcttggattc agatctcagc     780
tgcaagattg cccagctgcc cttgaccgga agcatgagta tcatcttctt cctgccctg      840 aaagtgaccc cagaatttga cttgatagag gagagcctca cctccgagtt cattcatgac     900
atagaccgag aactgaagac cgtgcaggcg gtcctcactg tccccaagct gaagctgagt     960
tacgaaggcg aagtcaccaa gtccctgcag gagatgaagc tgcaatcctt gtttgattca    1020
ccagacttta gcaagatcac aggcaaaccc atcaagctga ctcaggtgga acaccggggct   1080 ggctttgagt ggaacgagga tggggcggga accaccccca gcccagggct gcagcctgcc    1140
cacctcacct cccgctgga ctatcacctt aaccagcctt tcatcttcgt actgagggac    1200
acagacacag gggcccttct cttcattggc aagattctgg accccagggg cccctaa      1257

<210> SEQ ID NO 22
<211> LENGTH: 1257
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (681)..(681)
<223> OTHER INFORMATION: n = A or G

<400> SEQUENCE: 22
atgcaggccc tggtgctact cctctgcatt ggagccctcc tcgggcacag cagctgccag      60
aaccctgcca gccccccgga ggaaggctcc ccagaccccg acagcacagg ggcgctggtg     120
gaggaggagg atcctttctt caaagtcccc gtgaacaagc tggcagcggc tgtctccaac     180
ttcggctatg acctgtaccg ggtgcgatcc agcatgagcc ccacgaccaa cgtgctcctg     240
tctcctctca gtgtggccac ggccctctcg gccctctcgc tgggagcgga gcagcgaaca     300
gaatccatca ttcaccgggc tctctactat gacttgatca gcagcccaga catccatggt     360
acctataagg agctccttga cacggtcact gccccccaga gaacctcaa  gagtgcctcc     420 cggatcgtct ttgagaagaa gctgcgcata aaatccagct ttgtggcacc tctggaaaag     480
tcatatggga ccaggcccag agtcctgacg ggcaaccctc gcttggacct gcaagagatc     540
aacaactggg tgcaggcgca gatgaaaggg aagctcgcca ggtccacaaa ggaaattccc     600
```

```
gatgagatca gcattctcct tctcggtgtg gcgcacttca aggggcagtg ggtaacaaag    660
tttgactcca gaaagactga nctcgaggat ttctacttgg atgaagagag gaccgtgagg    720
gtccccatga tgtcggaccc taaggctgtt ttacgctatg gcttggattc agatctcagc    780
tgcaagattg cccagctgcc cttgaccgga agcatgagta tcatcttctt cctgcccctg    840
aaagtgaccc agaatttgac cttgatagag gagagcctca cctccgagtt cattcatgac    900
atagaccgag aactgaagac cgtgcaggcg gtcctcactg tccccaagct gaagctgagt    960
tacgaaggcg aagtcaccaa gtccctgcag gagatgaagc tgcaatcctt gtttgattca   1020
ccagacttta gcaagatcac aggcaaaccc atcaagctga ctcaggtgga acaccgggct   1080
ggctttgagt ggaacgagga tgggcggga accaccccca gcccagggct gcagcctgcc   1140
cacctcacct tcccgctgga ctatcacctt aaccagcctt tcatcttcgt actgagggac   1200
acagacacag gggcccttct cttcattggc aagattctgg accccagggg cccctaa      1257
```

VARIANTS OF PIGMENT EPITHELIUM DERIVED FACTOR AND USES THEREOF

RELATED APPLICATION DATA

This application is a continuation of U.S. patent application Ser. No. 11/718,873, filed May 8, 2007 and issued on May 8, 2012 as U.S. Pat. No. 8,173,591, which is the U.S. National Stage of International Application No. PCT/IL2004/001052, filed Nov. 16, 2004, the contents of each of which are herein expressly incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 64,686 byte ASCII (text) file named "Seq_List" created on Apr. 3, 2012.

FIELD OF THE INVENTION

The present invention provides anti-angiogenic variants of pigment epithelium derived factor (PEDF) comprising an altered phosphorylation site, polynucleotides encoding same and uses thereof. In particular, the variants of the invention provide improved anti-angiogenic activity while being devoid of certain undesirable properties of PEDF obtained from natural sources.

BACKGROUND OF THE INVENTION

Pigment epithelium derived factor (PEDF) was originally identified in conditioned medium of fetal human retinal pigment epithelium cell cultures. It shares sequence and structure homology to members of the superfamily of serine protease inhibitors (serpin), however, it does not serve as an inhibitor of any known protease activity.

PEDF was first described as a neurotrophic factor that induces a specific neuronal phenotype in retinoblastoma cells (Steel, F. R. et al. Proc. Natl. Acad. Sci. U.S.A. 90: 1526-1530, 1993). The neurotrophic activity of PEDF was also demonstrated by its ability to support neuronal survival (Taniwaki, T. et al. J. Neurochem. 64: 2509-2517, 1995), and its ability to protect neurons against neurotoxic effects. Structure-function studies have shown that this neurotrophic activity is exerted by the amino terminal segment (44-mer, amino acid residues 78-121) of the human PEDF, and that its activity is mediated through a ~80 kDa membranal receptor, which is abundant in retinoblastoma cells, and in neural retinal cells.

Besides its neurotrophic activity, PEDF was further demonstrated to be one of the most potent natural inhibitors of angiogenesis (Dawson, D. W. et al. Science 285: 245-248, 1999). Thus, it was found that PEDF inhibits not only bFGF-induced migration of endothelial cells under in vitro conditions, but also bFGF-induced neovascularization in an avascular rat cornea. Furthermore, addition of anti-PEDF antibodies (Abs) to rat corneas was found to stimulate the invasion of new vessels into these corneas, suggesting that PEDF plays a physiological regulatory role in retinal angiogenesis. PEDF was also shown to be a very potent inhibitor of neovascularization in a murine model of ischemia-induced retinopathy (Stellmach, V. V. et al. Proc. Natl. Acad. Sci. U.S.A. 98: 2593-2597, 2001). The anti-angiogenic activity of PEDF was associated with endothelial cell apoptosis, probably by increasing Fas ligand (FasL) mRNA and surface FasL in these cells.

It was recently reported that besides its expression in multiple sites in the eye, PEDF is also present in human plasma at a physiologically relevant concentration (Petersen, S. V. et al. Biochem. J. 374: 199-266, 2003). In the last decade several reports have described the possibility that protein kinases might function as a regulatory device not only intracellularly, but also in the cell exterior (Redegeld, F. A. et al. Trends Pharmacol. Sci. 20: 453-459, 1999). These reports described the presence of membrane-bound ectoprotein kinases (on the outer cell surface) and soluble secreted exoprotein kinases (detached from the cell). Additionally, it was shown that these ecto- or exoprotein kinases do have several substrates in the circulating blood including the coagulation cofactors Va and VIII as well as vitronectin. The main protein kinases that seem to exert exokinase activity are protein kinase A (PKA) and protein kinase CK2 (CK2). For example it was shown that vitronectin is phosphorylated by PKA and this phosphorylation modulate its interaction with PAI-1. In addition, phosphorylation by CK2 changes intracellular signaling by vitronectin, indicating that both PKA and CK2 play an important regulatory role in the circulating blood.

U.S. Pat. No. 5,840,686 to Chader et al., discloses nucleic acids that encode PEDF and a truncated PEDF, the equivalent proteins, and methods for producing recombinant PEDF and the truncated PEDF. U.S. Pat. No. 5,840,686 claims a method of prolonging neuronal cell survival and a method for inhibiting glial cell proliferation comprising administering recombinant PEDF. U.S. Pat. No. 6,319,687 to Chader et al., claims a recombinant PEDF protein (418 amino acids) and truncated forms of PEDF having neurotrophic as well as gliastatic activity.

PCT Application WO 01/58494 claims a method of treating an ocular-related disease in an animal. The method comprises expression of an angiogenesis inhibitor and a neurotrophic agent in an ocular cell using an expression vector that contains the nucleotide sequence for these factors. A preferred angiogenesis inhibitor is PEDF, which is known to exert both anti-angiogenic and neurotrophic activities.

U.S. Pat. No. 6,451,763 to Tombran-Tink et al., discloses the purification of PEDF from culture medium of human retinal pigment epithelial cells and claims methods of treating retinal diseases comprising administering PEDF to subjects in need thereof. It is also disclosed that in addition to retinal pigment epithelial cells, PEDF may be isolated from the vitreous humor of human, bovine, monkey and other primates. Since PEDF is abundant in the vitreous humor and since the vitreous humor is easily removed from the eyecup, the vitreous humor was suggested to be the easiest source from which PEDF can be isolated.

U.S. Pat. No. 6,797,691 to Bouck et al., discloses methods of inducing differentiation and slowing the growth of a neuroblastoma cell comprising administering PEDF to the cell.

International Patent Application WO 03/059248 discloses that PEDF is present in human plasma at physiologically relevant concentrations and exhibits potent anti-angiogenic and neurotrophic activities.

The inventors of the present application have shown that mutations of the phosphorylation sites of PEDF affected its anti-angiogenic and neurotrophic activities (Seger et al., The Weizmann Institute BioScience Open Day May 17, 2004; Seger et al., FEBS Lecture Course on Cellular Signaling, May 21-27, 2004; Seger et al., Blood, in press, 2004), but have not disclosed the utility of the present variants.

It would be highly advantageous to have PEDF variants having greater selectivity in terms of their anti-angiogenic and neurotrophic activity than native or wild-type PEDF.

SUMMARY OF THE INVENTION

The present invention provides anti-angiogenic variants of pigment epithelium derived factor (PEDF) of SEQ ID NO:1 comprising at least one altered phosphorylation site. The present invention further provides polynucleotides encoding the PEDF variants of the invention, expression vectors comprising same, and methods of treating diseases or disorders associated with neovascularization.

The present invention is based in part on the identification of PEDF phosphorylation sites. It is now disclosed, for the first time, that human PEDF undergoes casein kinase 2 (CK2) phosphorylation on the serine residues 24 and 114 and protein kinase A (PKA) phosphorylation on the serine residue 227.

Unexpectedly, substitution of the serine residues 24 and 114 by glutamic acid resulted in the production of a human PEDF variant, i.e., S24, 114E, having highly potent anti-angiogenic activity but essentially devoid of neurotrophic activity. The anti-angiogenic activity of the S24, 114E variant was higher than that obtained by the wild-type recombinant human PEDF or by the naturally occurring human PEDF, e.g., human plasma PEDF.

The PEDF variants are, therefore, very useful in treating diseases or disorders associated with neovascularization. It should be understood that the production of a PEDF variant is advantageous as large quantities of homogeneous anti-angiogenic PEDF are obtained. Additionally, the PEDF variants are essentially free from any disease-causing agents or any other undesirable proteins, which may accompany PEDF obtained from natural sources. It should also be appreciated that a PEDF variant having high anti-angiogenic activity but lower neurotrophic activity or even essentially devoid of neurotrophic activity compared to the recombinant wild-type PEDF is highly advantageous in treating diseases associated with neovascularization, particularly malignant conditions, where the neurotrophic activity of PEDF is undesirable.

According to one aspect, the present invention provides an anti-angiogenic variant of PEDF, an analog, or a fusion protein thereof comprising the amino acid sequence of SEQ ID NO:1 or a fragment thereof comprising at least one altered phosphorylation site.

According to some embodiments, the variant of PEDF, analog, fusion protein, or fragment thereof has lower neurotrophic activity compared to recombinant wild-type PEDF. According to some preferred embodiments, the variant of PEDF, analog, fusion protein, or fragment thereof is essentially devoid of neurotrophic activity.

According to additional embodiments, the at least one altered phosphorylation site of the PEDF variant, fragment, analog, or fusion protein thereof is selected from the group consisting of serine residues 24, 114, and 227. According to some embodiments, the PEDF variant, analog, or fusion protein thereof comprises an amino acid sequence selected from any one of SEQ ID NO:2 to SEQ ID NO:13 or a fragment thereof. According to other embodiments, the phosphorylation site is substituted by an amino acid selected from polar neutral amino acids, non-polar amino acids, negatively charged amino acids, and positively charged amino acids. According to currently preferred embodiments, the serine residue is substituted by a negatively charged amino acid, preferably by a glutamic acid. According to some embodiments, the present invention provides a PEDF variant, analog, or a fusion protein thereof, wherein the serine residue at position 24 is substituted by a glutamic acid, thus resulting in a PEDF variant of SEQ ID NO:2 or a fragment thereof. According to additional embodiments, the present invention provides a PEDF variant, analog, or a fusion protein thereof, wherein the serine residue at position 114 is substituted by a glutamic acid, thus resulting in a PEDF variant of SEQ ID NO:5 or a fragment thereof. According to yet other embodiments, the present invention provides a PEDF variant, analog, or a fusion protein thereof, wherein the serine residues at position 24 and 114 are substituted by glutamic acids, thus resulting in a PEDF variant of SEQ ID NO:8 or a fragment thereof.

According to some other embodiments, the serine residue of PEDF is altered by a chemical modification. Chemical modifications of an amino acid are well known in the art and include, but are not limited to, glycosylation, oxidation, permanent phosphorylation, reduction, myristylation, sulfation, acylation, acetylation, ADP-ribosylation, amidation, hydroxylation, iodination, methylation, and derivatization by protecting/blocking groups. Preferably, the chemical modification is permanent phosphorylation According to another aspect, the present invention provides an isolated polynucleotide sequence encoding an anti-angiogenic variant of PEDF, analog, or a fusion protein thereof, the anti-angiogenic variant of PEDF, analog, or fusion protein thereof comprising the amino acid sequence of SEQ ID NO:1 or a fragment thereof comprising at least one altered phosphorylation site.

According to some embodiments, the variant of PEDF, fragment, analog, or fusion protein thereof encoded by the isolated polynucleotide comprises at least one altered phosphorylation site, wherein the at least one altered phosphorylation site is selected from the group consisting of serine residues 24, 114, and 227. According to some embodiments, the isolated polynucleotide encodes a PEDF variant, analog, or a fusion protein thereof, the PEDF variant, analog, or fusion protein thereof comprising the amino acid sequence selected from any one of SEQ ID NO:2 to SEQ ID NO:13 or a fragment thereof. According to other embodiments, the serine residue is substituted to an amino acid other than serine. According to some embodiments, the isolated polynucleotide sequence is thus selected from any one of SEQ ID NO:15 to SEQ ID NO:22. According to currently preferred embodiments, the serine residue is substituted by a negatively charged amino acid, preferably by a glutamic acid. According to additional embodiments, the isolated polynucleotide sequence is selected from any one of SEQ ID NO:15, SEQ ID NO:16, SEQ ID NO:17, and SEQ ID NO:22 or a fragment thereof, which correspond to serine substitution by glutamic acid at position 24, 114, both 24 and 114, and 227, respectively.

According to a further aspect, the present invention provides an expression vector comprising an isolated polynucleotide sequence encoding an anti-angiogenic variant of PEDF, analog, or a fusion protein thereof, the anti-angiogenic variant of PEDF, analog, or fusion protein thereof comprising the amino acid sequence of SEQ ID NO:1 or a fragment thereof comprising at least one altered phosphorylation site.

According to yet another aspect, the present invention provides a host cell transfected with an expression vector according to the principles of the present invention.

According to a further aspect, the present invention provides a pharmaceutical composition comprising as an active ingredient an anti-angiogenic variant of PEDF, analog, or a fusion protein thereof, the PEDF variant, analog or fusion protein thereof comprising the amino acid sequence of SEQ ID NO:1 or a fragment thereof comprising at least one altered phosphorylation site according to the principles of the present invention, and a pharmaceutically acceptable carrier. The present invention further provides pharmaceutical compositions comprising as an active ingredient an isolated polynucleotide encoding an anti-angiogenic variant of PEDF, fragment, analog, or a fusion protein thereof according to the principles of the invention, and a pharmaceutically acceptable carrier.

According to another aspect, the present invention provides pharmaceutical compositions comprising as an active ingredient an expression vector comprising an isolated polynucleotide encoding an anti-angiogenic variant of PEDF, fragment, analog or fusion protein thereof according to the principles of the invention. According to some other embodiments, the pharmaceutical compositions of the invention comprise as an active ingredient a host cell transfected with an expression vector comprising an isolated polynucleotide encoding an anti-angiogenic variant of PEDF, fragment, analog, or fusion protein thereof according to the principles of the invention.

According to a further aspect, the present invention provides a method for treating a disease or disorder associated with neovascularization in a subject, the method comprising administering to the subject in need thereof a therapeutically effective amount of a pharmaceutical composition according to the principles of the invention.

According to some embodiments, the disease or disorder associated with neovascularization is selected from malignant and metastatic conditions, ocular disorders, and disorders treated with anti-angiogenic factors.

According to other embodiments, the disease or disorder associated with neovascularization is selected from the group consisting of sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor leiomydsarcoma, rhabdomyosarcoma, colon carcinoma, pancreatic cancer, breast cancer, ovarian cancer, prostate cancer, squamous cell carcinoma, basal cell carcinoma, adenocarcinoma sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, neovascular glaucoma, diabetic retinopathy, retinoblastoma, retrolental fibroplasias, uveitis, retinopathy of prematurity, macular degeneration, corneal graft neovascularization, retinal tumors, choroidal tumors, hemangioma, arthritis, psoriasis, angiofibroma, atherosclerotic plaques, hemophilic joints, and hypertrophic scars.

According to another aspect, the present invention provides a method for treating a neurodegenerative condition in a subject comprising administering to the subject in need thereof a therapeutically effective amount of a pharmaceutical composition according to the principles of the invention and a pharmaceutically acceptable carrier.

According to some embodiments, the neurodegenerative condition is selected from the group consisting of neurodegenerative diseases and other insults of the CNS (brain and retina), which are typified by death of neurons and overpopulation by glial cells (gliosis).

These and other embodiments of the present invention will be better understood in relation to the figures, description, examples and claims that follow.

BRIEF DESCRIPTION OF THE FIGURES

FIGS. 7A-B show the anti-angiogenic activity of the various rPEDF forms on bFGF-induced neovascularization in in vivo Matrigel plug assay. A, CD-1 nude mice were subcutaneously injected with Matrigel containing plPEDF or rPEDF forms in the presence or absence of bFGF. After 7 days, mice were sacrificed and Matrigel plugs were stained. Hematoxylin &Eosin staining of thin sections from Matrigel plugs are shown. B. Angiogenesis was measured by counting the number of blood vessels/field in each Matrigel plug. Student t-test was used to analyze statistical significance of the differences between plugs treated with bFGF and plugs treated with the combination of bFGF and the various PEDF forms (*P<0.01, **P<0.05).

DETAILED DESCRIPTION OF THE INVENTION

Figure 1A:
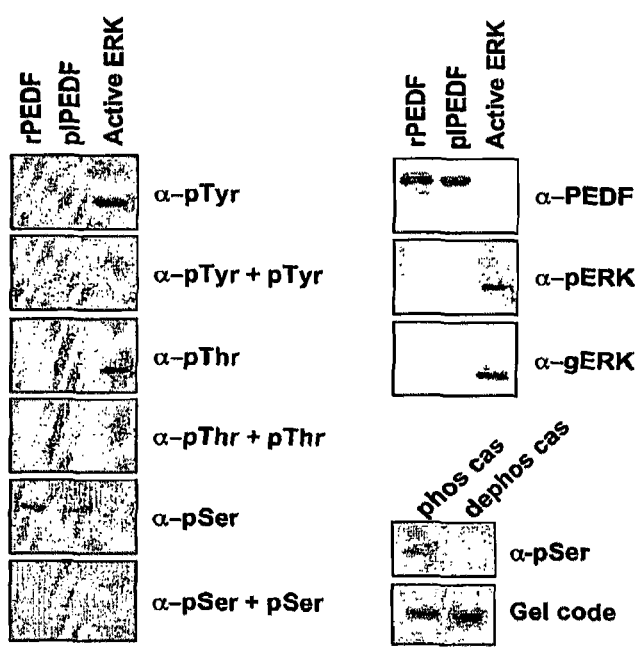
FIGS. 1A-D show that PEDF in plasma is a phosphoprotein. A, recombinant PEDF (rPEDF), plasma PEDF (plPEDF), active (phosphorylated) ERK, phosphorylated α-casein (phos cas) and dephosphorylated α-casein (dephos cas) were subjected to gel electrophoresis and immunoblotting with anti-phospho Ser, Thr, or Tyr Abs in the presence or absence of the appropriate phosphorylated amino acid. As a control, the samples were blotted with anti-PEDF, anti-phosphorylated ERK (αpERK) and anti-general ERK (αgERK) Abs, or stained with gel code for the α-casein. B, rPEDF or plPEDF were incubated in the absence or presence of alkaline phosphatase (APase) conjugated to beads. The samples: were subjected to in vitro CK2 or PKA phosphorylation. Phosphorylated products were analyzed by autoradiography (Auto, upper panel) or by immunoblotting with anti-PEDF Ab (lower panel). C, Quantitative analysis of the experiment depicted in FIG. 1B. D, Plasma PEDF was subjected to alkaline phosphatase treatment and incubated with fresh human plasma and $[\gamma^{32}P]$-ATP in the presence or absence of PKA inhibitor (PKI) or heparin. Control samples were subjected to in vitro CK2 or PKA phosphorylation. Vn—plasma vitronectin.

The present invention provides PEDF variants, fragments and analogs thereof comprising at least one altered phosphorylation site and having anti-angiogenic activity. The invention also provides isolated nucleic acids encoding PEDF variants, fragments and analogs thereof, the PEDF variants, fragments and analogs thereof comprising at least one altered phosphorylation site and having anti-angiogenic activity.

According to the present invention, the naturally occurring human PEDF of SEQ ID NO:1 contains two CK2 and one PKA phosphorylation sites. The CK2 phosphorylation sites reside on serine residues 24 and 114, while the PKA phosphorylation site resides on serine residue at position 227.

According to one aspect, the present invention provides an anti-angiogenic variant of PEDF, analog, or a fusion protein thereof comprising the amino acid sequence of SEQ ID NO:1 or a fragment thereof comprising at least one altered phosphorylation site.

According to some embodiments, the present invention provides a PEDF variant, fragment, analog, or a fusion protein thereof having reduced neurotrophic activity. According to some other embodiments, the PEDF variant, fragment or analog thereof being essentially devoid of neurotrophic activity.

According to yet other embodiments the variants of the invention retain neurotrophic activity and are useful in the treatment of neurodegenerative disease.

The term "fragment" as used herein refers to a peptide or polypeptide comprising only a portion of PEDF having anti-angiogenic activity. By "peptide" it is meant that the peptide comprises not more than 50 amino acids of PEDF. By "polypeptide" it is meant that the polypeptide generally comprises more than 50 amino acid residues of PEDF. It will be understood that though the present invention relates to human PEDF, since there is high homology between human PEDF and PEDF derived from other mammalian organisms, the present invention encompasses other mammalian PEDFs such as mouse, bovine, pig, and the like.

The term "anti-angiogenic" activity used herein is meant to define the ability of PEDF to reduce or inhibit endothelial cell proliferation and/or to reduce or inhibit endothelial cell migration and/or to induce endothelial cell apoptosis, and/or to reduce or inhibit neovascularization. Anti-angiogenic activity may be detected by various methods known in the art. Examples of in vitro and in vivo assays for angiogenic activity include mouse corneal neovascularization, chick chorioallantoic membrane assay, rabbit corneal pocket assay, aortic ring assay, and neovascularization in Matrigel plug assay (see also examples herein below).

The term "analog" as used herein refers to PEDF or fragments thereof, comprising altered sequences of PEDF of SEQ ID NO:1 by amino acid substitutions, additions, deletions, or chemical modifications. By using "amino acid substitutions", it is meant that functionally equivalent amino acid residues are substituted for residues within the sequence resulting in a silent change. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are known as conservative substitutions. Additionally, a non-conservative substitution may be made in an amino acid that does not contribute to the biological activity, e.g., anti-angiogenic activity or neurotrophic activity, of PEDF or a fragment thereof. It will be appreciated that the present invention encompasses PEDF analogs, wherein at least one amino acid is substituted by another amino acid to produce an anti-angiogenic analog of PEDF having increased stability or higher half life as compared to the naturally occurring PEDF or the wild-type recombinant PEDF.

The term "altered phosphorylation site" as used herein refers to alteration of a phosphorylation site by amino acid substitution and/or by chemical modification. It will be appreciated that substitution of a serine residue within a phosphorylation site as disclosed herein below is meant to refer to a conservative, but preferably to a non-conservative, substitution. Thus, substitution of a serine residue residing within a phosphorylation site such as within a CK2 or PKA phosphorylation site includes substitution to a non-polar amino acid, to negatively charged amino acid, or to a positively charged amino acid, preferably to a negatively charged amino acid.

Since phosphorylation of a serine residue within a protein is associated with addition of a negatively charged phosphate group to that serine, substitution of a serine by a negatively charged amino acid is useful to characterize the biological significance of that phosphorylation. Importantly, while a phosphorylated protein is dephosphorylated through the action of phosphatases in vivo, substitution of a serine with a negatively charged amino acid yields a protein having a permanent negatively charged amino acid at that site.

As shown herein below, substitution of the serine residue at position 24 of recombinant human PEDF by a glutamic acid or substitution of both serine residues 24 and 114 of recombinant human PEDF by glutamic acid reduced or abolished, respectively, PEDF neurotrophic activity as compared to the neurotrophic activity of recombinant wild-type (non-mutated) PEDF. Such variants, particularly the variant having glutamic acid at positions 24 and 114, were shown to have reduced or were even devoid of neurotrophic activity as compared to recombinant wild-type PEDF. In addition, substitution of serine residue 227 of recombinant human PEDF to alanine or to glutamic acid reduced PEDF neurotrophic activity as compared to the neurotrophic activity of recombinant wild-type PEDF. The present invention discloses, for the first time, a PEDF variant, which comprises two substitutions at positions 24 and 114 from serine to glutamic acid. The PEDF variant has significantly high anti-angiogenic activity and hardly any neurotrophic activity as compared to recombinant wild-type human PEDF. It is also disclosed that substitution of the ser residue 227 of recombinant human PEDF to glutamic acid reduced the anti-angiogenic activity of the variant as compared to the anti-angiogenic activity of recombinant wild-type human PEDF.

The term "neurotrophic" activity is defined herein as the ability to induce differentiation of a neuronal cell population. For example, PEDF's ability to induce differentiation in cultured retinoblastoma cells is considered neurotrophic activity. A PEDF variant, fragment, analog or a fusion protein thereof may be essentially devoid of neurotrophic activity. By referring to essentially devoid of neurotrophic activity it is meant to indicate that the PEDF variant, fragment, analog or fusion protein thereof has not more than 20% of the neurotrophic activity of recombinant wild-type PEDF, preferably not more than 10%, and more preferably not more than 5% of the neurotrophic activity of recombinant wild-type PEDF.

The present invention encompasses PEDF analogs of which at least one amino acid has been modified. Modifications of amino acid residues include, but are not limited to, glycosylation, oxidation, permanent phosphorylation, reduction, myristylation, sulfation, acylation, acetylation, ADP-ribosylation, amidation, cyclization, disulfide bond formation, hydroxylation, iodination, methylation, derivatization by protecting/blocking groups, or any other derivatization method known in the art. Such alterations, which do not destroy, but may improve the PEDF activity can occur anywhere along the sequence of the PEDF variant or a fragment thereof, including at the peptide backbone, the amino acid side-chains, the amino or carboxyl termini, but preferably at a phosphorylation site. It will be appreciated that the same type of modification may be present in the same or varying degrees at several sites in the protein.

The PEDF variants, PEDF fragments and analogs thereof comprising at least one altered phosphorylation site can be produced by various methods known in the art, including recombinant production or synthetic production. Recombinant production may be achieved by the use of an isolated polynucleotide encoding a PEDF variant, fragment or analog thereof, the isolated polynucleotide operably linked to a promoter for the expression of the polynucleotide. Optionally, a regulator of the promoter is added. The construct comprising the polynucleotide encoding the PEDF variant, fragment or analog thereof, the promoter, and optionally the regulator can be placed in a vector, such as a plasmid, virus or phage vector. The vector may be used to transfect or transform a host cell, e.g., a bacterial, yeast, insect, or mammalian cell.

The present invention also encompasses PEDF fragments produced by subjecting the PEDF variant to at least one cleavage agent. A cleavage agent may be a chemical cleavage agent, e.g., cyanogen bromide, or an enzyme, preferably an endoproteinase. Endoproteinases that can be used to cleave the PEDF variant include trypsin, chymotrypsin, papain, V8 protease or any other enzyme known in the art, which is known to produce proteolytic fragments.

Synthetic production of peptides or polypeptides is well known in the art and is available commercially from a variety of companies. A PEDF variant, fragment or an analog thereof comprising at least one altered phosphorylation site can be synthesized using standard direct peptide synthesis (e.g., as summarized in Bodanszky, 1984, Principles of Peptide Synthesis (Springer-Verlag, Heidelberg), such as via solid-phase synthesis (see, e.g., Merrifield, 1963, J. Am. Chem. Soc. 85:2149-2154). Examples of solid phase peptide synthesis methods include the BOC method, which utilized tert-butyloxcarbonyl as the α-amino protecting group, and the FMOC method, which utilizes 9-fluorenylmethyloxcarbonyl to protect the α-amino of the amino acid residues, both methods are well-known by those of skill in the art. Furthermore, if desired, non-classical amino acids or chemical amino acid analogs can be introduced as a substitution or addition into a PEDF variant, fragment or analog thereof. Non-classical amino acids include, but are not limited to, oc-aminoisobutyric acid, 4-aminobutyric acid, hydroxyproline, sarcosine, citrulline, cysteic acid, t-butylglycine, t-butylalanine, phenylglycine, cyclohexylalanine, and the like.

The invention should further be construed to include a PEDF variant, fragment or analog thereof, which may contain one or more D-isomer forms of the amino acids of PEDF. Production of a retro-inverso D-amino acid PEDF peptide where the peptide is made with the same amino acids as disclosed, but at least one amino acid, and perhaps all amino acids are D-amino acids is a simple matter once armed with the present invention. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein.

Included within the scope of the invention are chimeric, or fusion proteins comprising a PEDF variant, a fragment or analog thereof joined at its amino or carboxy-terminus or at one of the side chains via a peptide bond to an amino acid sequence of a different protein. Such chimeric proteins can be made by protein synthesis, e.g., by use of a peptide synthesizer, or by ligating the appropriate nucleic acid sequences encoding the desired amino acid sequences to each other by methods known in the art, in the proper coding frame, and expressing the chimeric protein by methods commonly known in the art.

According to another aspect, the present invention provides an isolated polynucleotide sequence encoding a PEDF variant, a fragment, analog, or a fusion protein thereof comprising at least one altered phosphorylation site, the PEDF variant, fragment, analog, or fusion protein thereof having anti-angiogenic activity. The term "PEDF variant" used throughout the specification and claims should be construed to include all forms of active PEDF variants that comprise at least one altered phosphorylation site and having anti-angiogenic activity.

The term "polynucleotide" means a polymer of deoxyribonucleic acid (DNA) or ribonucleic acid (RNA), which can be derived from any source, can be single- or double-stranded, and can optionally contain synthetic, non-natural, or altered nucleotides, which are capable of being incorporated into DNA or RNA polymers.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence, and RNA such as mRNA.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

One who is skilled in the art will appreciate that more than one nucleic acid may encode any given protein in view of the degeneracy of the genetic code and the allowance of exceptions to classical base pairing in the third position of the codon, as given by the so-called "Wobble rules." Moreover, polynucleotides that include more or less nucleotides can result in the same or equivalent proteins. Accordingly, it is intended that the present invention encompass all polynucleotides that encode the amino acid sequences of SEQ ID NO:2 to SEQ ID NO:13, as well as analog proteins. The present invention also encompasses polynucleotides with substitutions, additions, or deletions, which direct the synthesis of the PEDF variant, fragment, analog, or a fusion protein thereof.

Polynucleotide sequences which encode wild type or native PEDF polypeptides are known (see, e.g., published International Patent Applications WO 95/33480 and WO 93/24529); see also GenBank accession no. U29953), and others can be deduced from the polypeptide sequences discussed herein. According to specific embodiments, the present invention provides polynucleotide sequences encoding PEDF variants, the polynucleotides selected from any one of SEQ ID NO:15 to SEQ ID NO:22.

The PEDF polynucleotides may be expressed as a transported protein where the PEDF variant is isolated from the medium in which the host cell containing the polynucleotide is grown, or may be expressed as an intracellular protein by deleting the leader or other peptides, in which case the PEDF is isolated from the host cells. The PEDF so isolated is then purified by protein purification methods known in the art.

PEDF polypeptides can be provided to the tissue of interest by transferring an expression vector comprising an isolated polynucleotide encoding a PEDF variant, fragment or analog thereof to cells associated with the tissue of interest. The cells produce and secrete the PEDF polypeptide such that it is suitably provided to endothelial cells within the tissue to attenuate or inhibit angiogenesis within the tissue of interest. Thus, the expression vectors comprising a PEDF variant typically include isolated polynucleotide sequences which are homologous to known PEDF sequences, e.g., they will hybridize to at least a fragment of the known sequences under at least mild stringency conditions, more preferably under moderate stringency conditions, most preferably under high stringency conditions (employing the definitions of mild, moderate, and high stringency as set forth in Sambrook et al., 1989, Molecular Cloning: A Laboratory Manual, 2d edition, Cold Spring Harbor Press).

In addition to the isolated polynucleotide sequences encoding PEDF variant polypeptides, the expression vectors comprise a promoter. In the context of the present invention, the promoter must be able to drive the expression of the PEDF polynucleotide within the cells. Many viral, promoters are appropriate for use in such an expression cassette (e.g., retroviral ITRs, LTRs, immediate early viral promoters (IEp) (such as herpes virus IEp (e.g., ICP4-IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters). Other suitable promoters are eukaryotic promoters, which contain enhancer sequences (e.g., the rabbit β-globin regulatory elements), constitutively active promoters (e.g., the β-actin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the polynucleotide encoding the PEDF variant and the promoter are operably linked such that the promoter is able to drive the expression of the PEDF variant polynucleotide. As long as this operable linkage is maintained, the expression vector can include more than, one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vectors must be introduced into the cells in a manner such that they are capable of expressing the isolated polynucleotide encoding a PEDF variant, a fragment or analog thereof contained therein. Any suitable vector can be so employed, many of which are known in the art. Examples of such vectors include naked DNA vectors (such as oligonucleotides or plasmids), viral vectors such as adeno-associated viral vectors (Berns et al., 1995, Ann. N.Y. Acad. Sci. 772: 95-104), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640), papilloma virus vectors, picornavirus vectors, polyoma virus vectors, retroviral vectors, SV40 viral vectors, vaccinia virus vectors, and other vectors. In addition to the expression vector of interest, the vector can also include other genetic elements, such as, for example, genes encoding a selectable marker (e.g., β-gal or a marker conferring resistance to a toxin), a pharmacologically active protein, a transcription factor, or other biologically active substance.

Methods for manipulating a vector comprising an isolated polynucleotide are well known in the art (see, e.g., Sambrook et al., supra) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The PEDF expression vector is introduced into the cells by any means appropriate for the transfer of DNA into cells. Many such methods are well-known in the art (Sambrook et al., supra; see also Watson et al., 1992, Recombinant DNA, Chapter 12, 2d edition, Scientific American Books). Thus, in the case of prokaryotic cells, vector introduction may be accomplished, for example, by electroporation, transformation, transduction, conjugation, or mobilization. For eukaryotic cells, vectors may be introduced through the use of, for example, electroporation, transfection, infection, DNA coated microprojectiles, or protoplast fusion.

Cells into which the PEDF variant polynucleotide has been transferred under the control of an inducible promoter if necessary, can be used as transient transformants. Such cells themselves may then be transferred into a mammal for therapeutic benefit therein. Typically, the cells are transferred to a site in the mammal such that the PEDF variant expressed therein and secreted therefrom contacts the desired endothelial cells in order that angiogenesis is inhibited. Alternatively, particularly in the case of cells to which the vector has been added in vitro, the cells may first be subjected to several rounds of clonal selection (facilitated usually by the use of a selectable marker sequence in the vector) to select for stable transformants. Such stable transformants are then transferred to a mammal for therapeutic benefit therein.

The PEDF variant may also be provided to the endothelial cells by transfecting into a population of other cells a vector comprising an isolated polynucleotide encoding a PEDF variant according to the invention, whereby the PEDF variant is expressed in and secreted from said other cells. The population of other cells so transfected is then transferred to a site in the mammal where PEDF variant so secreted contacts the endothelial cells and inhibits angiogenesis. Expression and secretion of PEDF variant from the other cells then has benefit on the endothelial cells. It is not necessary that the DNA encoding PEDF be stably integrated into the cells. PEDF may be expressed and secreted from non-integrated or from integrated DNA in a cell.

Within the cells, the PEDF polynucleotide is expressed such that the cells express and secrete the PEDF variant polypeptide. Successful expression of the polynucleotide can be assessed using standard molecular biological techniques (e.g., Northern hybridization, Western blotting, immunoprecipitation, enzyme immunoassay, etc.). Reagents for detecting the expression of PEDF genes and the secretion of PEDF from transfected cells are known in the art (see also examples herein below).

The PEDF variants produced by recombinant techniques may be purified so that the PEDF variant will be substantially pure when administered to a subject. The term "substantially pure" refers to a compound, e.g., a protein or polypeptide, which has been separated from components, which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

Pharmaceutical Compositions and Administration Routes

The present invention provides pharmaceutical compositions comprising a therapeutically effective amount of a PEDF variant, a fragment or analog thereof having anti-angiogenic activity and a pharmaceutically acceptable carrier, the PEDF variant, fragment or analog thereof comprising at least one altered phosphorylation site.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned.

The compositions can take the form of solutions, suspensions, emulsion, tablets, pills, capsules, powders, sustained-release formulations and the like. The composition can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of an anti-angiogenic PEDF variant, a fragment or analog thereof, preferably in a substantially purified form, together with a suitable amount of carrier so as to provide the form for proper administration to the subject.

The amount of the anti-angiogenic PEDF variant, a fragment or analog thereof which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test bioassays or systems.

Depending on the location of the tissue of interest, the PEDF variant can be supplied in any manner suitable for the provision of PEDF to endothelial cells within the tissue of interest. Thus, for example, a composition containing a source of PEDF variant (i.e., a PEDF variant polypeptide, or an isolated polynucleotide encoding a PEDF variant, or a PEDF variant expression vector, or cells expressing PEDF variant, as described herein above) can be introduced into the systemic circulation, which will distribute the source of PEDF to the tissue of interest. Alternatively, a composition containing a source of PEDF can be applied topically to the tissue of interest (e.g., injected, or pumped as a continuous infusion, or as a bolus within a tumor, applied to all or a portion of the surface of the skin, dropped onto the surface of the eye, etc.).

Methods of introduction of a pharmaceutical composition comprising a source of PEDF variant include, but are not limited to, topical, intradermal, intramuscular, intraperitoneal, intravenous, subcutaneous, intranasal, epidural, ophthalmic, and oral routes. The compounds may be administered by any convenient route, for example by infusion or bolus injection, by absorption through epithelial linings (e.g., oral mucosa, rectal and intestinal mucosa, etc.), and may be administered together with other therapeutically active agents. It is preferred that administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some preferred embodiments, administration can be by direct injection e.g., via a syringe, at the site of a tumor or neoplastic or pre-neoplastic tissue.

For topical application, an anti-angiogenic PEDF variant can be combined with a pharmaceutically acceptable carrier so that an effective dosage is delivered, based on the desired activity (i.e., ranging from an effective dosage, for example, of 1.0 pM to 1.0 mM to attenuate or prevent localized angiogenesis). In one embodiment, an anti-angiogenic PEDF variant is applied to the skin for treatment of diseases such as psoriasis. The carrier may be in the form of, for example, and not by way of limitation, an ointment, cream, gel, paste, foam, aerosol, suppository, pad or gelled stick A topical composition for treatment of some of the eye disorders comprises an effective amount of an anti-angiogenic PEDF in a ophthalmologically acceptable excipient such as buffered saline, mineral oil, vegetable oil such as corn or arachis oil, petroleum jelly, and Miglyol 182, alcohol solutions, or liposomes or liposome-like products. These compositions may also include preservatives, antioxidants, antibiotics, immunosuppressants, and other therapeutically effective agents, which do not exert a detrimental effect on the anti-angiogenic PEDF variant.

For directed internal topical applications, the pharmaceutical composition may be in the form of tablets or capsules, which cap contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to materials of the above type, a liquid carrier such as a fatty oil. In addition, dosage unit forms can contain various other materials which modify the physical form of the dosage unit, for example, coatings of sugar, shellac, or other enteric agents.

An anti-angiogenic PEDF variant, a fragment or analog thereof can be delivered in a controlled release system. In one embodiment, an infusion pump may be used to administer an anti-angiogenic PEDF variant, a fragment or analog thereof, such as for example, that is used for delivering insulin or chemotherapy to specific organs or tumors (see Buchwald et al., 1980, Surgery 88: 507; Saudek et al., 1989, N. Engl. J. Med. 321: 574). In a preferred form, an anti-angiogenic PEDF variant is administered in combination with a biodegradable, biocompatible polymeric implant, which releases the anti-angiogenic PEDF variant over a controlled period of time at a selected site. Examples of preferred polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Uses of PEDF

The present invention provides a method for treating diseases or disorders, particularly diseases or disorders associated with neovascularization. The method of treatment comprises administering to a patient in need thereof a pharmaceutical composition comprising as an active ingredient a therapeutically effective amount of a PEDF source and a pharmaceutically acceptable carrier. The PEDF source according to the present invention includes a PEDF polypeptide, e.g., the anti-angiogenic PEDF variant, a fragment, analog, or a fusion protein thereof; an isolated polynucleotide sequence encoding the PEDF polypeptides of the invention; an expression vector comprising the isolated polynucleotide sequence encoding the PEDF polypeptides of the invention;

and a host cell transfected with an expression vector comprising an isolated polynucleotide sequence encoding the PEDF polypeptides of the invention.

The inhibition of angiogenesis is generally considered to be the halting of the development of new blood vessels, whether they develop by sprouting or by the arrival and subsequent differentiation into endothelial cells of circulating stem cells. However, since PEDF can induce apoptosis of activated endothelial cells, inhibition of angiogenesis in the context of the present invention should also be construed to include the killing of cells by PEDF, particularly cells in existing vessels near or within a tumor. Thus, within the context of the present invention, inhibition of angiogenesis should be construed to include inhibition of the development of new vessels, which inhibition may or may not be accompanied by the destruction of nearby existing vessels. The terms "neovascularization" and angiogenesis are used interchangeably throughout the specification and claims.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

Patients in need thereof may suffer from one or more disease or disorder associated with neovascularization or may have been determined to have a greater susceptibility to a disease or disorder associated with neovascularization. Thus, the method of treatment according to the present invention includes both therapeutic and prophylactic utility.

Neovascular diseases and disorders that can be treated with anti-angiogenic PEDF include malignant and metastatic conditions including, but not limited to, solid tumors such as sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor leiomydsarcoma, rhabdomyosarcoma, colon carcinoma, pancreatic cancer, breast cancer, ovarian cancer, prostate cancer, squamous cell carcinoma, basal cell carcinoma, adenocarcinoma sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, and retinoblastoma.

Ocular disorders associated with neovascularization which can be treated with an anti-angiogenic PEDF variant, a fragment or analog thereof include, but are not limited to, neovascular glaucoma, diabetic retinopathy, retinoblastoma, retrolental fibroplasias, uveitis, retinopathy of prematurity, macular degeneration, corneal graft neovascularization as well as other eye inflammatory diseases, ocular tumors such as retinal tumors and choroidal tumors, and diseases associated with retinal, choroidal or iris neovascularization.

Other disorders, which can be treated with an anti-angiogenic PEDF variant include, but are not limited to, hemangioma, arthritis, psoriasis, angiofibroma, atherosclerotic plaques, hemophilic joints, and hypertrophic scars.

An anti-angiogenic PEDF variant can be tested in vivo for the desired therapeutic or prophylactic activity as well as for determination of a therapeutically effective dosage. For example, such compounds can be tested in suitable animal model systems prior to testing in humans, including, but not limited to, rats, mice, chicken, cows, monkeys, rabbits, and the like. For in vivo testing, prior to administration to humans, any animal model system known in the art may be used (see examples herein below).

According to another aspect, the present invention provides a method for treating a neurodegenerative diseases or condition in a subject comprising administering to the subject in need thereof a therapeutically effective amount of a pharmaceutical composition according to the principles of the invention and a pharmaceutically acceptable carrier.

"Neurotrophic" activity is defined herein as the ability to induce differentiation of a neuronal cell population. For example, PEDF's ability to induce differentiation in cultured retinoblastoma cells is considered neurotrophic activity. "Neuronotrophic" activity is defined herein as the ability to enhance survival of neuronal cell populations. For example, PEDF's ability to act as a neuron survival factor on neuronal cells is neuronotrophic activity. "Gliastatic" activity is defined herein as the ability to inhibit glial cell growth and proliferation. For example, PEDF's ability to prevent growth and/or proliferation of glial cells is gliastatic activity.

Many neurodegenerative diseases and other insults to the CNS (brain and retina) are typified by death of neurons and overpopulation by glia (gliosis). PEDF can be used effectively in these conditions to prolong the life and functioning of the primary neurons and to stave off the glial advance. PEDF can be effective, for example, in blocking microglial activation in response to CNS injury as well as prolonging/sparing the lives of neurons. In the retina, it is predictable that PEDF inhibits the Muller glial cells. Since Muller cells are similar to astroglia, PEDF would be similarly effective in blocking gliosis in conditions such as retinal detachment, diabetes, Retinitis Pigmentosa, etc. as well as sparing the lives of the retinal neurons.

It is thought that transplantation of neurons may cure certain pathologies. For example, in Parkinson's disease, transplantation of specific fetal brain cells into patients could alleviate or cure the problems associated with the disease. One of the major problems to contend with, though, would be to prolong the life of the transplanted cells and to keep them differentiated, e.g. secreting the proper substances, etc. Pretreatment of the cells with PEDF could aid in both of these areas. Similarly, transfection of either neurons or astroglia with the PEDF gene before implantation can be a long-term source of PEDF at the transplantation site.

There is much activity in attempts at transplantation of neural retina and photoreceptor cells to help cure blindness. Attempts to date have not been fruitful both due to non-differentiation and death of the grafts. PEDF may help in both regards. Specifically, photoreceptor neurons to be transplanted can be pretreated with PEDF or the gene transfected into the cells before surgery. Alternatively, PEDF can be transfected at high levels into adjacent retinal pigment epithelial (RPE) cells where they can serve as a supranormal source of the protein. Several investigators have now shown that cultured RPE cells survive very well after transplantation into the interphotoreceptor space of test animals. Transfection of human RPE cells in vitro with the PEDF gene the use of these cells in retinal transplantation is, therefore, feasible.

Where PEDF is produced naturally, it can be present in concentrations as high as about 250 nM. Because PEDF variants are non-toxic, they can be supplied to tissues in a far more concentrated dosage. However, given PEDF variant's potency, it can be employed at far reduced concentrations, such as about 10 nM or less (e.g., as little as 0.01 nM). Depending on the formulation of a composition comprising the PEDF source, it is supplied over a time course sufficient to retard angiogenesis and/or to induce neuronal cell differentiation, i.e., neurotrophic activity, and/or to improve neuronal cell survival, i.e., neuronotrophic activity, and/or to inhibit glial cell proliferation, i.e, gliastatic activity within a desired tissue.

In some protocols, repeated application may enhance the anti-angiogenic activity and/or the neurotrophic and/or neuronotrophic and/or gliastatic activity of the PEDF variant and may be required in some applications. Where the source of PEDF is a PEDF expression vector, the cells expressing PEDF may produce an effective amount of the protein (i.e., sufficient to exert one or more of the biological activities of PEDF).

PEDF variants can be administered alone or in conjunction with other therapeutic modalities. It is appropriate to administer a PEDF variant as part of a treatment regimen involving other therapies, such as surgery, drug therapy, photodynamic therapy, and/or radiation therapy.

EXAMPLES

Reagents and Antibodies

Recombinant human CK2 was purchased from Calbiochem (Darmstadt, Germany), the catalytic subunit of PKA was purified as previously described. Active ERK was purified as described. Full-length human PEDF cDNA was provided by Dr. N. Bouck (Northwestern University, Chicago, Ill., USA). Phosphothreonine Ab was purchased from Zymed Laboratories, Inc (San Francisco, Calif.). Phosphotyrosine Ab (PY99) was purchased from Santa Cruz Biotechnology (Santa Cruz, Calif.) pERK, gERK phosphoserine Abs, bFGF, α-casein and dephosphorylated casein were purchased from Sigma (Rehovot, Israel). Polyclonal Ab against PEDF was developed by the Ab Unit of the Weizmann Institute of Science.

Cell Cultures

Human Y-79 retinoblastoma cells (ATCC, Manassa, Va.) were grown in MEM supplemented with 2 mM L-Glutamine and 15% fetal calf serum (FCS). HEK-293T cells were cultured in DMEM F-12 supplemented with 10% FCS. HUVEC were grown in M-199 supplemented with 20% FCS, 25 µg/ml ECGS mitogen (BT-203, Biomedical Technologies Inc, Stoughton, Mass.), and 5 U/ml heparin.

Construction of rPEDF Variants

Full-length PEDF cDNA was used as a template for oligonucleotide-site directed mutagenesis kit (Clontech, Palo Alto, Calif.). Pure PCR products digested by Hind III and EcoR I were ligated into the multicloning site of pcDNA3. DNA sequencing analysis confirmed the nucleotide sequence of the PEDF variants.

Transient Expression of Variants in HEK-293T Cells pcDNA3 carrying variants were introduced into HEK-293T cells using the LipofectAMINE reagent (Life Technologies Inc, Grand Island, N.Y.) according to the manufacturer's instructions. The transfected cells were serum starved (3 days, serum-free) after which the PEDF variants were purified on a $Ni^{+2}$ column (Amersham, UK) according to the manufacturer's instructions.

Purification of PEDF from Human Plasma plPEDF was purified from human citrated plasma (1 L) by a 9-20% PEG cut followed by DEAE-Sephacel column (2.9×40 cm) and heparin agarose column that was developed stepwise. The fractions were pooled (~20 ml), dialyzed against buffer D (20 mM Tris-HCl, pH 7.4), and applied onto a Mono Q-FPLC column (1 ml, Pharmacia, Sweden), which was developed with a linear NaCl gradient in buffer D. PEDF was eluted at 0.2M NaCl and usually yielded 1 mg pure PEDF (4° C. all steps).

Alkaline Phosphatase Treatment of PEDF

Recombinant PEDF (50 µg/ml) or plPEDF (50 µg/ml) were incubated with alkaline phosphatase conjugated to acrylic beads (50 U/ml) or with sepharose CL-4B beads as control (45 min, 30° C.). Beads were pre-equilibrated with BSA (1 mg/ml), Tris-HCl (50 mM pH 8.0), and EDTA (0.1 mM). Reaction was arrested by centrifugation. The supernatant was further subjected to an in vitro phosphorylation.

In Vitro Phosphorylation of PEDF

The phosphorylation assay (40 µl) contained either rPEDF, plPEDF or rPEDF variants (50 µg/ml). For CK2: the constituents were CK2 (4 µg/ml), glycerol (2%), NaCl (20 mM), β-mercaptoethanol (0.1 mM), $MgCl_2$ (20 mM), $[\gamma^{32}P]$-ATP (10 µM), poly-L-lysine (200 nM), and Tris-HCl (50 mM pH 7.4). For PKA: pure catalytic subunit of PKA (2.5 µg/ml), $MgCl_2$ (10 mM), heparin (50 µg/ml), $[\gamma^{32}P]$-ATP (14M), and Tris-HCl (50 mM pH 6.5). For human plasma: phosphatase treated PEDF (30 µg/ml), fresh human plasma, $MgCl_2$ (20 mM), $[\gamma^{32}P]$-ATP (24M), Tris (50 mM pH 7.4) with or without PKA inhibitor (PKI, 1 µg/ml) or heparin (100 µg/ml). Reactions were for 45 min at 30° C. Then, boiled sample buffer was added, and the samples were subjected to 10% SDS-PAGE.

Determination of ERK Phosphorylation

Serum starved cells were treated with rPEDF, plPEDF or the various rPEDF variants (10 nM unless otherwise specified) for the indicated times. Following stimulation pERK and gERK were detected using the appropriate Abs.

Neurite Outgrowth Assay

Human Y-79 retinoblastoma cells were assayed for neurite outgrowth. Briefly, one ml of a Y-79 cell suspension ($2.5 \times 10^5$ cells/ml) was incubated with rPEDF, plPEDF or with the various rPEDF variants (20 nM) in the cell's medium. After 7 days the cells were transferred to poly-D-lysine coated plates, and their neurite outgrowth was monitored by light microscopy at various periods of time.

Aortic Ring Assay

The aortic ring assay was performed as follows: thoracic aortas were dissected from 10-12 weeks old BALB/C mice and transferred to Petri dish containing BIO-MPM-1. After removing excess perivascular tissue, transverse cuts of 1 mm long were made. The rings were embedded in collagen mix (7 parts collagen, 1 part 10×MEM, and 2 parts 0.15M $NaHCO_3$, 800 µl) in 24-well plates. Medium (500 µl BIO-MPM-1 containing penicillin-streptomycin and the examined reagent) was added to the embedded rings, and the plates were incubated at 37° C. in a humidified incubator. Medium containing reagents was replaced 3 times a week. After 10-12 days, the rings were fixed with 4% formaldehyde and stained with crystal violet (0.02%). The effect of each factor was examined in 2 wells (4 rings) per assay, and was repeated at least 3 times.

Matrigel Plug Angiogenesis Assay

Matrigel (BD Biosciences, MA; 0.5 ml/mouse) containing bFGF (300 ng/ml), with or without PEDF (20 nM) was injected subcutaneously into the flank of 8 weeks old nude mice as described by Passaniti, A. et al. (Lab. Invest. 67: 519-528, 1992). On day 7, mice were sacrificed, plugs were removed, fixed (4% formaldehyde), paraffin embedded and sectioned. Sections were stained using Hematoxylin-Eosin (H&E). Endothelial cells/microvessels infiltrating the Matrigel were confirmed by Masson's Trichrome staining.

Example 1

PEDF in Plasma is a Phosphoprotein

PEDF, which was identified as a neurotrophic and antiangiogenic factor in the eye, was recently found to be present also in circulating blood. Since it was demonstrated that exokinases are able to phosphorylate plasma proteins, the experiment aimed at studying whether PEDF can be a target for phosphorylation by these kinases. Two forms of PEDF were used in the study: (1) PEDF purified from human plasma (plPEDF); and (2) recombinant PEDF (rPEDF), which was expressed in HEK-293T cells and purified from the serum free medium of these cells. To examine whether plPEDF is indeed a phosphoprotein, plPEDF and rPEDF were first immunoblotted with various anti-phospho amino acid Abs. Both proteins were specifically recognized by anti-phospho-Ser Ab, but not by anti-phospho-Thr, or by anti-phospho-Tyr Abs (FIG. 1A). As positive controls, active phosphorylated ERK (pERK), which was recognized both by anti-phospho-Tyr and anti-phospho-Thr, and a casein, which was recognized only by anti-phospho-Ser Ab, were used. The results indicated that plPEDF and rPEDF are phosphorylated on Ser residue(s).

Figure 1B:
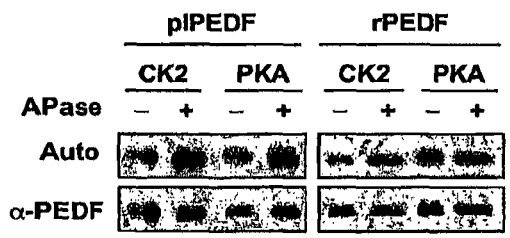
Figure 1C:
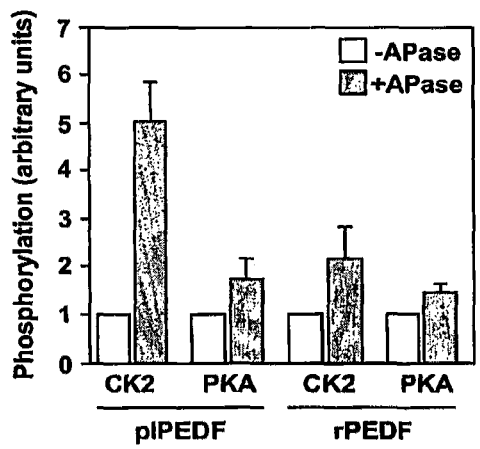

The existence of extracellular PICA and CK2 activities is well documented. Analysis of the primary amino acid sequence of PEDF revealed the existence of several putative phosphorylation sites for CK2, as well as for PICA. In order to examine whether PEDF can be phosphorylated by one of these protein kinases, rPEDF and plPEDF were pretreated with immobilized alkaline phosphatase prior to an in vitro phosphorylation reaction by CK2 and PKA. Phosphorylated products were subjected to SDS-PAGE followed by Western blotting, and the membranes were first exposed to autoradiography and then immunoblotted with anti-PEDF Ab. Pretreatment of plPEDF with alkaline phosphatase (FIG. 1B) significantly increased CK2, and to a lesser extent PKA phosphorylation of the protein. The PKA and CK2 phosphorylation of rPEDF following phosphatase treatment were also increased, but not as significantly as plPEDF (FIG. 1C).

Figure 1D:
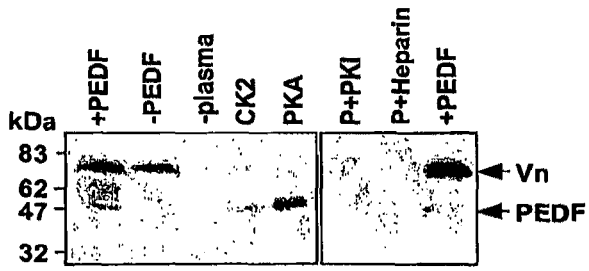

To further verify that CK2 phosphorylation of PEDF can occur in plasma, plPEDF was pretreated with alkaline phosphatase following its phosphorylation by fresh human plasma. A phosphorylated product that corresponds exactly to PEDF was detected by the autoradiography (FIG. 1D left panel). Heparin, which is an inhibitor of CK2, and PKI, which inhibits PKA, inhibited this reaction (FIG. 1D, right panel). Taken together, our results indicate that PEDF is phosphorylated in the circulating blood on the CK2 sites. The small amount of phosphorylation in the secreted rPEDF may be a result of cellular phosphorylation.

Example 2

CK2 and PICA Phosphorylate PEDF in Vitro

Figure 2A:
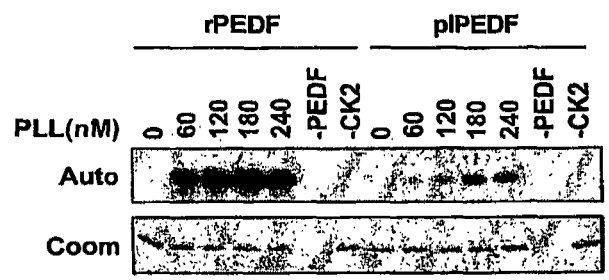
FIGS. 2A-E show the CK2 and PKA phosphorylation of PEDF in vitro. A, rPEDF and plPEDF were incubated with CK2, $[\gamma^{32}P]$-ATP and increasing concentrations of poly-L-lysine (PLL). The samples were subjected to gel electrophoresis. The gel was stained with Coomassie blue (Coom, lower panel), and subjected to autoradiography (Auto, upper panel). B, rPEDF and plPEDF were incubated with CK2, $[\gamma^{32}P]$-ATP, poly-L-lysine, and increasing concentrations of heparin (Hep). Phosphorylation was detected by autoradiography. C, rPEDF and plPEDF were incubated with the catalytic subunit of PKA, heparin, and $[\gamma^{32}P]$-ATP. Phosphorylation was detected by autoradiography. D, rPEDF was digested with trypsin for the indicated time periods. The samples were subjected to gel electrophoresis followed by silver staining of the gel (left panel). rPEDF was radioactively phosphorylated by CK2 and then subjected to trypsin digestion and to gel electrophoresis followed by autoradiography. E, Schematic representation of PEDF showing the CK2 and PKA phosphorylation sites and the tryptic peptides revealed by mass spectrometry and N-terminus sequence analysis.
Figure 2B:
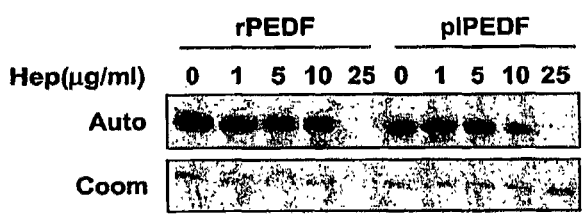

As plPEDF is found to be a phosphoprotein that can be phosphorylated by CK2 and PKA, the phosphorylation of plPEDF by these kinases was next analyzed. Thus, rPEDF and plPEDF were incubated with CK2 and $[\gamma^{32}P]$-ATP, with an increasing concentration of poly-L-lysine, which activates CK2 in vitro. Both rPEDF and plPEDF were phosphorylated by CK2 (FIG. 2A), and as reported for calmodulin, the phosphorylation of PEDF was dependent on the presence of poly-L-lysine. Additionally, CK2 phosphorylation of rPEDF was stronger than the phosphorylation of plPEDF (FIG. 2A), indicating that some of the plPEDF CK2 phosphorylation sites are already phosphorylated. Heparin was found to inhibit CK2 phosphorylation of PEDF (FIG. 2B).

Figure 2C:
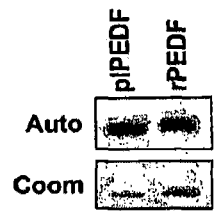

The possibility that PEDF is an in vitro substrate of PKA was also determined. rPEDF and plPEDF were incubated with the pure catalytic subunit of PKA and $[\gamma^{32}P]$-ATP in the presence of heparin, which stimulates PKA phosphorylation of several substrates. Both rPEDF and plPEDF were equally phosphorylated by PKA in the presence of heparin (FIG. 2C) in a PKI-inhibited manner (not shown), indicating that both proteins contain only a small amount of phosphate incorporated to the PKA site.

Example 3

Localization of the CK2 Phosphorylation Site(s) in PEDF

CK2 phosphorylates Ser or Thr immersed in acidic sequence within proteins and peptides. The minimum requirement for CK2 phosphorylation is depicted by the sequence S/T-X-X-D/E. The presence of additional Asp or Glu residues at positions −3, +1, +2, +4, +5, or +7 improves the phosphorylation efficacy. By examining the primary sequence of PEDF for potential phosphorylation sites, 11 putative sites that meet the minimal consensus requirements were found. These are S24, S114, T121, S195, T219, T226, S227, T287, S328, 5336, and T354. Of these, S24, S114, S195, T226, S227 and T287 were considered as preferred targets since they contain additional acidic residues in the preferred positions.

Figure 2D:
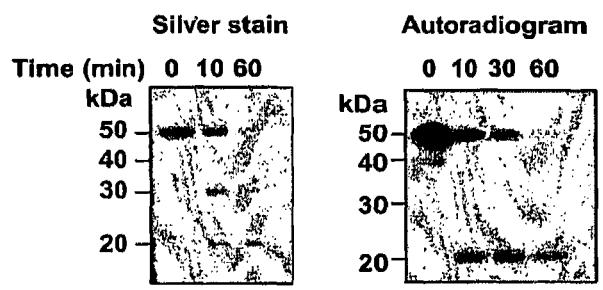
Figure 2E:
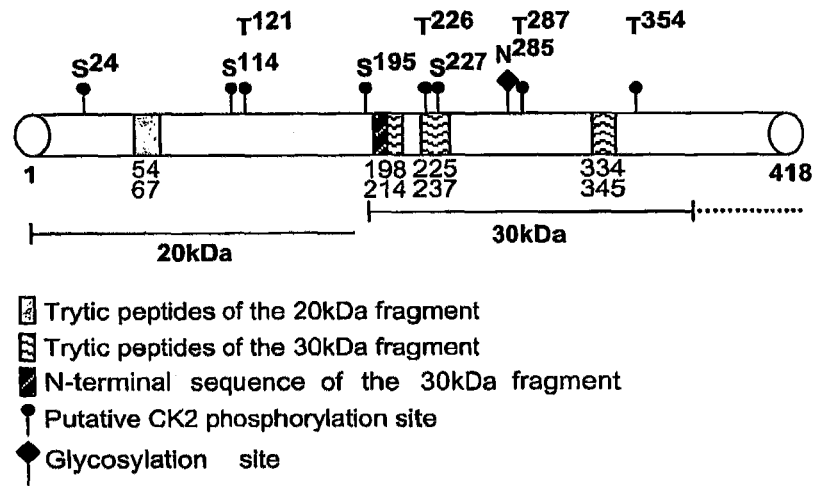

In an attempt to identify the actual CK2 phosphorylation site(s) in PEDF, rPEDF was digested with trypsin. This partial digestion yielded two major fragments with an apparent molecular weight of 20 kDa and 30 kDa (FIG. 2D). We then phosphorylated rPEDF by CK2 and digested the phosphorylated protein with trypsin. Only the 20 kDa fragment was phosphorylated by CK2 (FIG. 2D), indicating that the CK2 phosphorylation site is located within the 20 kDa fragment. The fragment could not be sequenced by Edman degradation since it was blocked, indicating that it is the N-terminal fragment of PEDF. The 30 kDa fragment was sequenced by Edman degradation and was found to start at amino acid Glu198. Mass spectrometry revealed more peptides in the 30 kDa fragment (FIG. 2E) confirming its C-terminal position. Since the CK2 phosphorylation sites are located within the 20 kDa fragment, it was concluded that Ser24 and/or Ser114 are the sites of CK2 phosphorylation. However, because the combined mass of the fragments is smaller than that of the full-length rPEDF, it is possible that an additional CK2 phosphorylated fragment, which run out of the gel, was also formed.

Example 4

Figure 3A:
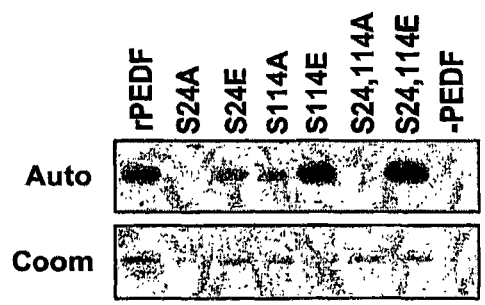
FIGS. 3A-C show the identification of CK2 and PKA phosphorylation sites of PEDF by site directed mutagenesis. A, rPEDF and rPEDF variants were radioactively phosphorylated by CK2. The samples were subjected to gel electrophoresis. The gel was stained with Coomassie blue (Coom, lower panel), and subjected to autoradiography (Auto, upper panel). B, rPEDF and rPEDF variants were radioactively phosphorylated by PKA. Samples were subjected to gel electrophoresis. The gel was stained with Coomassie blue (Coom, lower panel), and subjected to autoradiography (Auto, upper panel). C, Quantitative analysis of the autoradiogram depicted in FIGS. 3A and B.

Identification of the CK2 Phosphorylation Site(s) by Site Directed Mutagenesis To further study the CK2 phosphorylation sites in PEDF, single or double site variants were constructed by replacing Ser at position 24, 114 with Ala (S24A, S114A and S24, 114A) or with Glu (S24E, S114E and S24,114E). rPEDF and its variants were purified from the medium of the transfected HEK-293T cells and subjected to phosphorylation by CK2. Mutation of S24A significantly reduced CK2 phosphorylation (FIG. 3A), while the S24E mutation reduced phosphorylation only to a moderate extent (FIG. 3A). The S114A variant significantly reduced CK2 phosphorylation, while the double variant S24,114A almost completely abolished this phosphorylation (FIG. 3A). It was concluded that both Ser24 and Ser114 are the main sites for CK2 phosphorylation of PEDF. Surprisingly, both S114E and S24,114E mutations significantly increased CK2 phosphorylation compared with CK2 phosphorylation of rPEDF (FIG. 3A). This unexpected result implies that mutation of this residue to Glu probably leads to the exposure of additional potential phosphorylation sites that were normally covered. Analysis of the three dimensional structure of PEDF revealed that Thr121 is spatially close to Ser114 and may serve as the additional site. However, since this site may be covered upon phosphate incorporation to Ser24 and Ser114, it is possible that Thr354 is the other phosphorylated site. This site might have been phosphorylated by CK2 but was not detected in the tryptic digest because it was included in a small fragment that was not present on the gels. Nonetheless, our results indicate that PEDF is phosphorylated by CK2 mainly on residues Ser24 and Ser114.

Example 5

Identification of the PKA Phosphorylation Site by Site Directed Mutagenesis

Figure 3B:
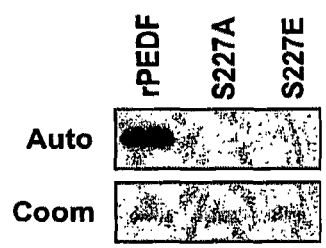
Figure 3C:
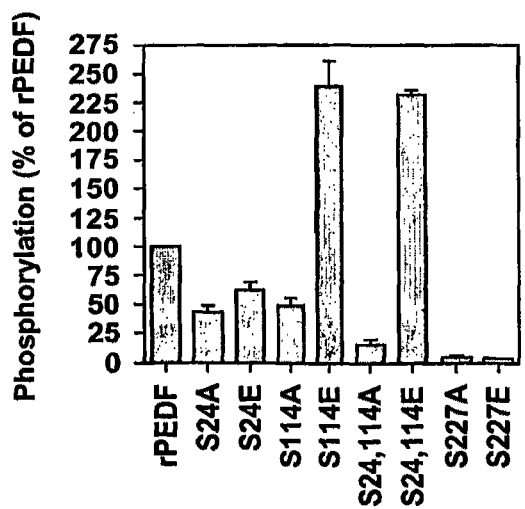

PICA phosphorylates Ser or Thr residues adjacent to at least two consecutive basic residues, depicted by the consensus sequence of R/K-R/K-X-S/T. By examining the primary sequence of PEDF for potential PKA phosphorylation sites, one such putative site at Ser227 was found. In order to confirm this PKA phosphorylation site in PEDF, a single site variant was constructed by replacing Ser227 either with Ala (S227A) or with Glu (S227E). The rPEDF and the variants were purified as described herein above and subjected to phosphorylation by PKA. Mutation of Ser227 to Ala or to Glu completely abolished PKA phosphorylation of both rPEDF and plPEDF (FIG. 3B), indicating that this residue is indeed the PKA site in PEDF.

A three dimensional structure analysis of the CK2 and PKA phosphorylation sites in PEDF revealed that Ser114 and Ser227 residues are exposed and can be accessible to interact with potential kinases. Ser24 is not included in the crystal structure, however the location of the N-terminus is spatially converging to Ser114. Therefore, from the structural point of view, these residues may well serve as substrate candidates for phosphorylation.

Example 6

Activation of ERIC by PEDF in Endothelial Cells

Figure 4A:
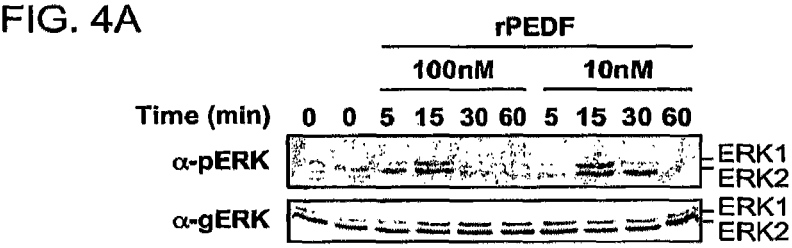
FIGS. 4A-E show the effect of rPEDF, plPEDF and the various rPEDF variants on ERK/MAPK activation in HUVEC. A, Endothelial cells (HUVEC) were stimulated with 10 and 100 nM of rPEDF. Cytosolic extracts were subjected to immunoblotting with anti-phosphorylated ERK (αpERK, upper panel) or anti-general ERK (αgERK, lower panel) Abs. B, HUVEC were stimulated with rPEDF or with plPEDF. Cytosolic extracts were subjected to immunoblotting with anti-pERK Ab (pERK, upper panel) or with anti-gERK Ab (gERK, lower panel). C and D, HUVEC were stimulated with rPEDF, plPEDF, or with the various rPEDF variants. Cytosolic extracts were subjected to immunoblotting as described above in panel A. E, Quantitative analysis of immunoblots depicted in panels C and D.
Figure 4B:
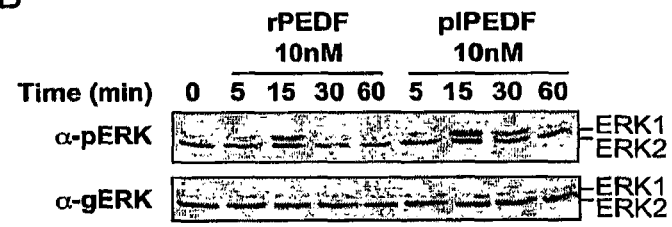

The effect of PEDF and its phosphorylated forms on the signaling and physiological responses of endothelial cells was next studied. Therefore, serum-starved endothelial cells were incubated with rPEDF or with plPEDF, and cell lysates were analyzed for MAPKs and PKB activity using anti-phospho Abs. PKB as well as JNK, p38MAPK or ERK5 were not significantly affected in any of the conditions used (not shown). On the other hand, rPEDF caused a small (×5) but reproducible activation of ERK phosphorylation in endothelial cells, whether the cells were obtained from a human source (e.g., HUVEC; FIG. 4A) or from a bovine source (e.g., BAEC; not shown). The maximal activation of ERK1/2 was obtained after 15 min with 10 nM PEDF. Interestingly, the activation obtained with plPEDF was higher than that with rPEDF in HUVEC (FIG. 4B) as well as in BAEC (not shown).

Example 7

The Effect of rPEDF Variants on ERK Activation

Figure 4C:
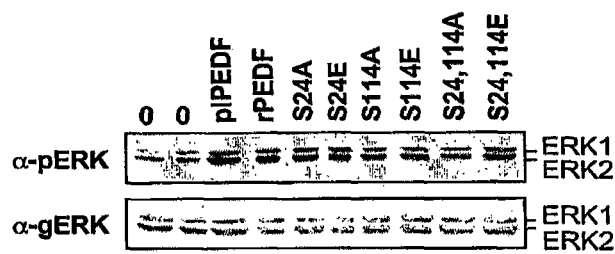

Because of the differences in ERK activation between plPEDF and rPEDF, ERK activation system was used to examine whether the phosphorylation variants indeed mimic the effect of phosphorylation on PEDF activity. When used to stimulate HUVEC, the CK2 phosphorylation site variants S24A and S24E did not have a significant effect, while S114A and S114E variants demonstrated slightly reduced ability to stimulate ERK phosphorylation (FIG. 4C). However, significant effects were found with the double variants, as S24,114A had a reduced effect, while S24,114E enhanced ERK phosphorylation (FIG. 4C). These effects were even stronger than the effects of rPEDF or plPEDF respectively. The higher activity of S24,114E suggests that the two Glu residues indeed mimic the activity of phosphorylated PEDF. However, plPEDF is incompletely phosphorylated in contrast to the existence of negatively charged residues at positions 24 and 114 of all molecules of the S24,114E. Similarly, the activity of S24,114A was lower than that of rPEDF suggesting that a small fraction of the rPEDF molecules is phosphorylated on Ser 24 and 114. Thus, the variants S24,114E and S24,114A further extent the phosphorylation-dependent differences between plPEDF and rPEDF.

Figure 4D:
Figure 4E:
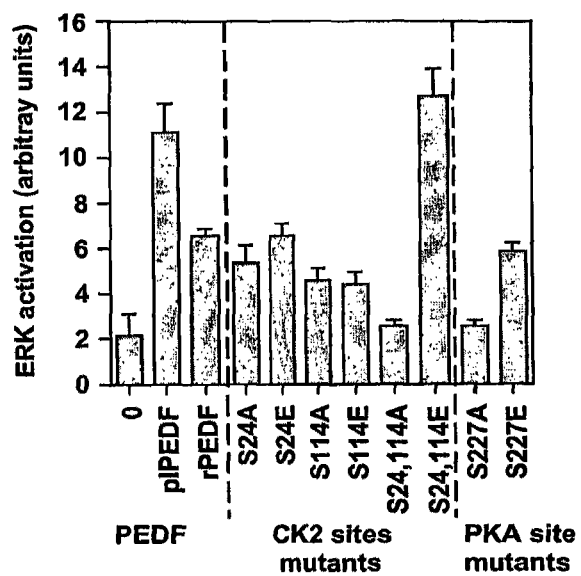

Differences in ERK activation were observed also with the PKA variants. Thus, S227A completely inhibited the ability of rPEDF to induce. ERK1/2 phosphorylation, whereas the S227E variant had only a slight inhibitory effect (FIG. 4D). Similar results were obtained with BAEC (not shown). These results further indicate that rPEDF is secreted as a phosphorylated protein on residue 227, in agreement with the phosphatase study above. Removal of the phosphate abolishes the PEDF-induced ERK phosphorylation, while Glu at this position elevated the PEDF effect. Taken together, our results indicate that the Glu or Ala variants indeed mimic the phosphorylated or non-phosphorylated forms of PEDF.

Example 8

The Effect of rPEDF Variants on its Neurotrophic Activity

Figure 5A:
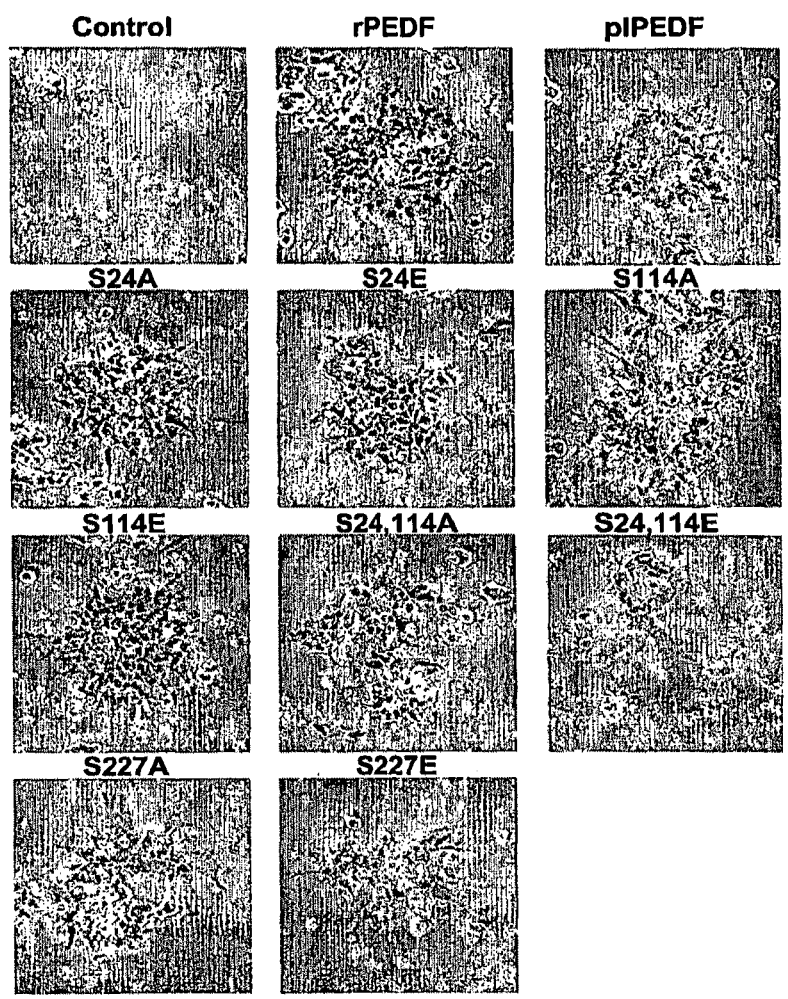
FIGS. 5A-B show the effect of rPEDF, plPEDF and the various rPEDF variants on PEDF neurotrophic activity. Retinoblastoma cells were incubated with rPEDF, plPEDF, or with the various rPEDF variants and differentiation at 10 days post-attachment is shown. B. Quantitative analysis of the results presented in panel A. Student t-test was used to analyze statistical significance of the differences between cells treated with rPEDF and cells treated with the various PEDF forms (*P<0.01, **P<0.050).
Figure 5B:
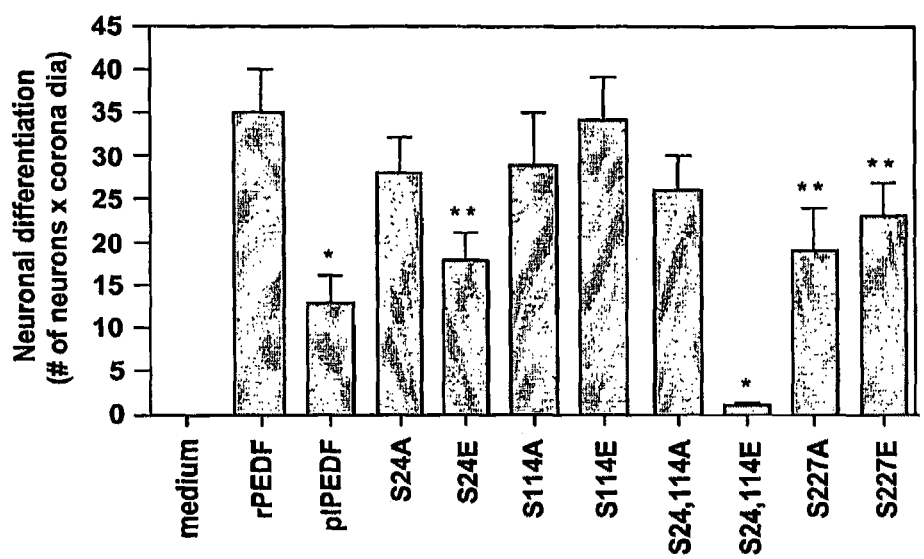

It was then aimed at studying whether CK2 as well as PKA phosphorylation of PEDF can modulate its neurotrophic activity. For that end, rPEDF, plPEDF and the various variants were used to examine their ability to induce differentiation in human retinoblastoma Y-79 cells in culture. Indeed, rPEDF and plPEDF induced neuronal differentiation (cell aggregation and neurite outgrowth) in Y-79 cells, where the effect of rPEDF was more pronounced compared to plPEDF (FIG. 5). The CK2 phosphorylation site variants S24E/S24A and S114E/S114A had only small effects, as they all induced neuronal differentiation of the Y-79 cells. However, much less neurite-like processes and cell aggregates were observed when cells were treated with the S24,114E variant. With this variant, the cells formed small corona-like structures but were very compact without any sprouts projecting from the cells, and this inhibitory effect was stronger than that of plPEDF (FIG. 5). On the other hand, cells treated with the S24,114A variant exhibit neurite outgrowth and big aggregates similar to rPEDF (FIG. 5). Mutation of the PKA phosphorylation site S227E revealed a different phenotype, where colonies were smaller, fewer and randomly spread, although their processes were clearly observed. Therefore, PKA phosphorylation has a limited influence on the neurotrophic effect of PEDF while CK2 phosphorylation significantly reduces this neurotrophic effect.

Example 9

The Ex-Vivo Anti-Angiogenic Activity of rPEDF Variants

Figure 6A:
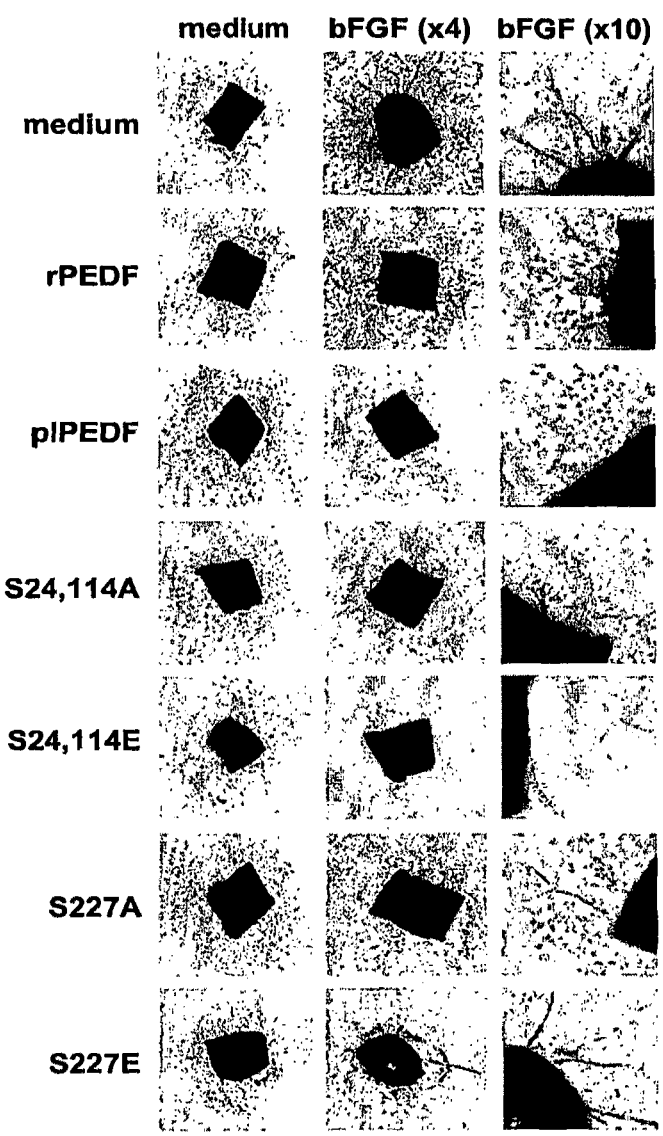
FIGS. 6A-B show the anti-angiogenic activity of the various rPEDF forms on bFGF-induced vessel sprouting in the ex-vivo aortic ring assay. A, Aortic rings were exposed to plPEDF or to the various rPEDF forms in the presence or absence of bFGF. The rings were stained with crystal violet to illustrate sprouting and vessels formation. Micrographs were taken under ×4 and ×10 objective. B. Quantitative analysis of the assay described in panel A. Student t-test was used to analyze statistical significance of the differences between rings treated with bFGF and rings treated with the combination of bFGF and the various PEDF forms. (*P<0.01).
Figure 6B:
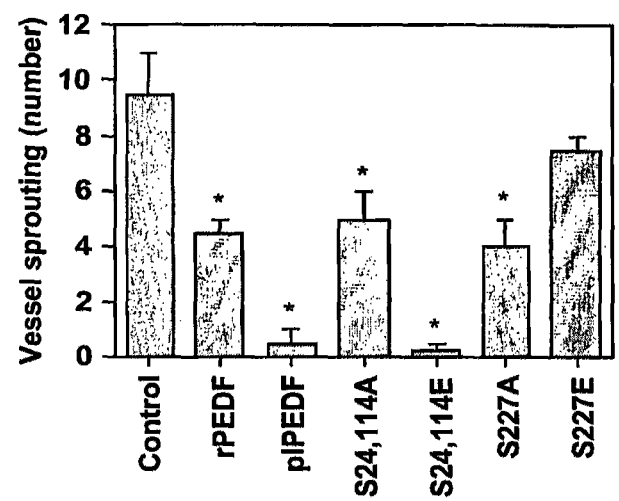

To examine the effect of phosphorylation, on the antiangiogenic activity of PEDF, the ex-vivo aortic ring assay in the presence of bFGF was used as an angiogenic model. In the presence of bFGF (50 ng/ml), aortic rings from BALB/C mice developed numerous vessels-like sprouts as compared to the rings that were treated with serum free medium (FIG. 6). As expected, plPEDF significantly inhibited the bFGF-induced vessel formation. However, the inhibitory effect of rPEDF was less pronounced than that of plPEDF, as rearrangement towards vessel formation and small number of vessels structure were observed when rPEDF and bFGF were added together.

The anti-angiogenic activity of the PEDF variants was then examined. When incubated together with bFGF, the CK2 non-phosphorylated double variant, S24,114A, exhibited an antiangiogenic activity that was similar to or slightly less then that of rPEDF, where rearrangement towards vessels could be seen, but clear vessels were not formed (FIG. 6). On the other hand, the CK2 phosphorylated variant, S24,114E, appeared to be a very potent antiangiogenic factor, even stronger than plPEDF, as it did not allow any vessel formation (FIG. 6). The PKA non-phosphorylated variant, S227A, inhibited the bFGF-induced vessel formation similarly to rPEDF, while the PKA phosphorylated variant, S227E, had less antiangiogenic activity (FIG. 6). S227E alone was not proangiogenic and its effect on, the bFGF-induced angiogenesis was reduced as compared to rPEDF. It was, therefore, concluded that phosphorylation of PEDF on its CK2 sites significantly enhanced the antiangiogenic activity of PEDF, while the phosphorylation on its PKA site may slightly reduce its antiangiogenic activity.

Example 10

The In Vivo Anti-Angiogenic Activity of rPEDF Variants

Figure 7B:
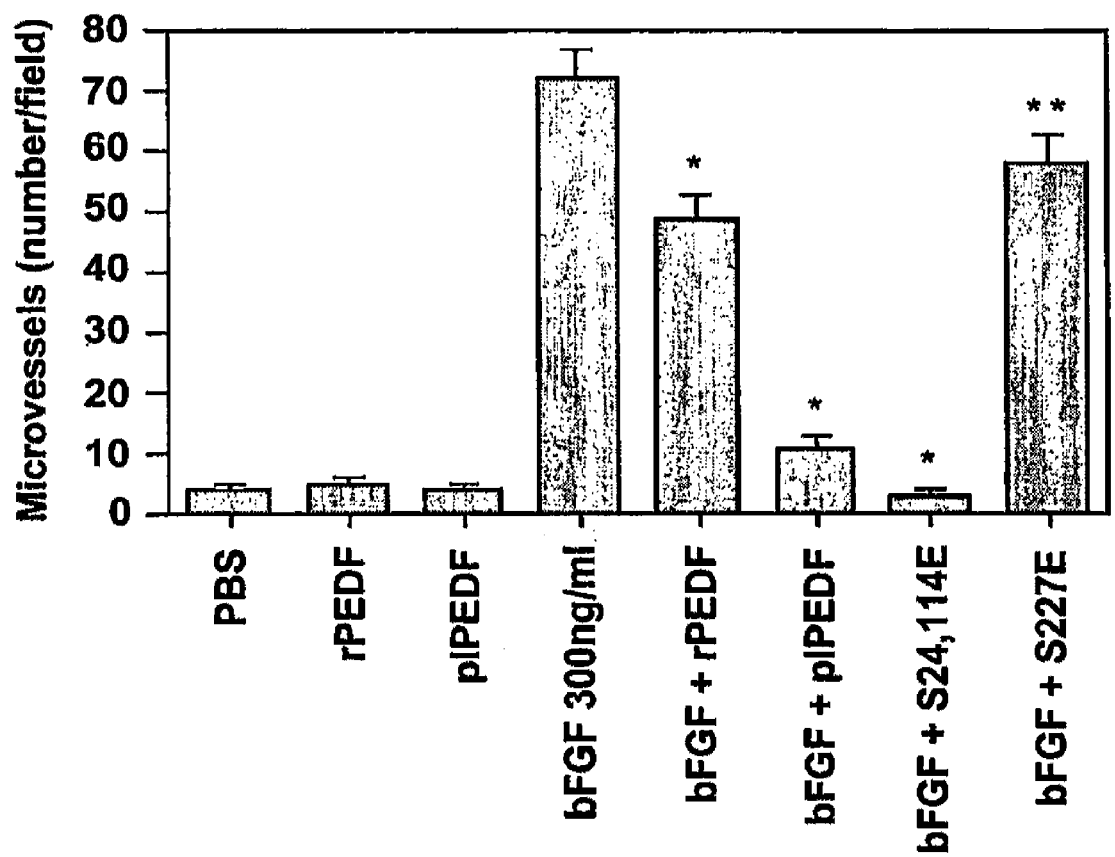

To further assess the effect of phosphorylation on PEDF anti-angiogenic activity in vivo the Matrigel plug assay in the presence of bFGF was used as an angiogenic model. Thus, liquid Matrigel supplemented with the various treatments was injected subcutaneously into CD-1 nude mice. The Matrigel polymerized to form a plug, which was removed after a week and analyzed for its angiogenic response. As expected, control plugs treated with PBS or PEDF alone showed very little angiogenic response (FIG. 7). bFGF-impregnated plugs elicited a robust angiogenic activity, as judged by the large number of blood vessels infiltrating into the plug (FIG. 7). plPEDF significantly inhibited the bFGF-induced vessel infiltration, while the inhibitory effect of rPEDF was significantly less pronounced (FIG. 7). As was shown in the aortic ring assay, the S24,114E variant had even stronger antiangiogenic activity relative to plPEDF, as plugs treated with this variant had very little angiogenic response (FIG. 7). In contrast, plugs treated with bFGF and S227E had much less antiangiogenic activity reflected in many infiltrating vessels (FIG. 7). In addition plugs treated with bFGF and S24,114A variant or S227A variant appeared similar to those treated with bFGF and rPEDF (not shown). These results further indicate that CK2 phosphorylation enhances the antiangiogenic activity of PEDF, while the phosphorylation on its PKA site may reduce this activity.

Example 11

Prevention of Angiogenesis of the Anterior Chamber of the Eye by Systemic Administration of PEDF Variants Four rats (250 gr each) are given three intraperitoneal injections of a PEDF variant (750 µg per dose in 5 ml water containing 3.5% ethanol) at four-day intervals. The following day the animals are anesthetized with xylazine-ketamine and angiogenesis is induced by inoculating 2 ml heparanase (30 mg/ml) into the frontal compartment of the eye in the cornea of one of the two eyes in each rat. A fourth intraperitoneal injection of 750 µg the PEDF variant is applied the next day. Two positive control animals receive only 2 ml heparanase (30 mg/ml) into the frontal compartment of the eye. Angiogenesis is then allowed to develop for 5 days at which time animals are anesthetized with xylazine-ketamine, examined and photographed under a binocular microscope for development of blood vessels in the anterior chamber of the eye. In the control eye, blood vessels appear after heparanase-induced angiogenesis, while in the eye of a PEDF variant-treated rat blood vessels are absent. Similar protection is obtained when angiogenesis is induced in rat eyes with bFGF.

Example 12

PEDF Variants Inhibit the Growth of Metastases

Tumor growth and specifically the ability of tumors to metastasize is angiogenesis dependent. Lewis lung carcinoma metastases are treated systemically with PEDF variants. Animals with Lewis lung carcinomas of 600-1200 mm$^3$ tumors are sacrificed and the skin overlying the tumor is cleaned with betadine and ethanol. In a laminar flow hood, tumor tissue is excised under aseptic conditions. A suspension of tumor cells in 0.9% normal saline is made by passage of viable tumor tissue through a sieve and a series of sequentially smaller hypodermic needles of diameter 22- to 30-gauge. The final concentration is adjusted to $1 \times 10^7$ cells/ml and the suspension is placed on ice. After the site is cleaned with ethanol, the subcutaneous dorsa of mice in the proximal midline are injected with $1 \times 10^6$ cells in 0.1 ml of saline.

When tumors are 1500 mm$^3$ in size, approximately 14 days after implant, the mice undergo surgical removal of the primary tumor. The incision is closed with simple interrupted sutures. From the day of operation, mice receive daily subcutaneous injections of a PEDF variant at a dose of 0.3 mg/kg/day or of saline. When the control mice become sick from metastatic disease (typically after 13 days of treatment), all mice are sacrificed and autopsied. Lung surface metastases are counted by means of a stereomicroscope at 4× magnification. Lung weight, which reflects tumor burden, is measured in the PEDF variant treated and in the control mice. Further, weight loss is also measured as a means to evaluate toxicity in any of the mice treated with PEDF variants.

It will be appreciated by persons skilled in the art that the present invention is not limited by what has been particularly shown and described herein above. Rather the scope of the invention is defined by the claims that follow.

The invention claimed is:

1. An isolated variant of pigment epithelium derived factor (PEDF) or a fragment or a fusion protein thereof, said variant comprising the amino acid sequence as set forth in any one of SEQ ID NOs:2-7 and 11-13, wherein the variant differs from the wild-type PEDF of SEQ ID NO:1 by having a substitution for serine at amino acid residue 24, 114, or 227, wherein the fragment or fusion protein includes said substitution, and wherein the variant or the fragment or the fusion protein has anti-angiogenic activity.

2. The isolated variant of PEDF, or the fragment or fusion protein thereof, according to claim 1 having reduced neurotrophic activity compared to recombinant wild-time PEDF.

3. The isolated variant of PEDF, or the fragment or fusion protein thereof, according to claim 1 having neurotrophic activity of up to 20% of the neurotrophic activity of wild-type PEDF.

4. The isolated variant of PEDF, or the fragment or fusion protein thereof, according to claim 1, wherein the serine residue is substituted by a negatively charged amino acid.

5. The isolated variant of PEDF, or the fragment, or fusion protein thereof, according to claim 4, wherein the serine residue is substituted by a glutamic acid.

6. A pharmaceutical composition comprising as an active ingredient the isolated variant of pigment epithelium derived factor (PEDF), the fragment or the fusion protein thereof according to claim 1, and a pharmaceutically acceptable carrier.

7. A method for inhibiting neovascularization in a subject having a disease or disorder characterized by increased neovascularization comprising administering to said subject a therapeutically effective amount of the pharmaceutical composition according to claim 6.

8. The method according to claim 7, wherein the disease or disorder is selected from the group consisting of a malignant disease, a metastatic disease, and macular degeneration.

* * * * *